(12) United States Patent
Davis et al.

(10) Patent No.: US 9,233,893 B2
(45) Date of Patent: Jan. 12, 2016

(54) SELECTIVE HYDROGENATION OF ALKYNYL-CONTAINING COMPOUNDS AND POLYUNSATURATED COMPOUNDS

(75) Inventors: S. Mark Davis, Humble, TX (US); Paul F. Keusenkothen, Houston, TX (US); Charles J. Mart, Baton Rouge, LA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 516 days.

(21) Appl. No.: 13/571,120

(22) Filed: Aug. 9, 2012

(65) Prior Publication Data

US 2013/0204055 A1    Aug. 8, 2013

Related U.S. Application Data

(60) Provisional application No. 61/527,367, filed on Aug. 25, 2011.

(51) Int. Cl.
*C07C 5/09*    (2006.01)

(52) U.S. Cl.
CPC .......................................... *C07C 5/09* (2013.01)

(58) Field of Classification Search
CPC ................ C07C 5/02; C07C 5/08; C07C 5/09
USPC .................. 585/259, 258, 261, 275
See application file for complete search history.

(56) References Cited

U.S. PATENT DOCUMENTS

| | | | |
|---|---|---|---|
| 3,242,223 A * | 3/1966 | Helmut Nonnenmacher et al. | 585/541 |
| 4,705,906 A | 11/1987 | Brophy et al. | |
| 5,382,748 A * | 1/1995 | Behrmann et al. | 585/899 |
| 7,153,807 B2 | 12/2006 | Molinier et al. | |
| 7,404,936 B2 * | 7/2008 | Mazanec et al. | 422/198 |
| 7,692,051 B2 * | 4/2010 | Johnson et al. | 585/259 |

FOREIGN PATENT DOCUMENTS

| | | |
|---|---|---|
| EP | 1 405 664 | 4/2004 |
| FR | 651037 | 2/1929 |
| FR | 2231640 | 12/1974 |

OTHER PUBLICATIONS

A.N.R. Bos et al., "Mechanism and kinetics of the selective hydrogenation of ethyne and ethene", Chemical Engineering and Processing, 32 (1993), pp. 1-7.

* cited by examiner

*Primary Examiner* — In Suk Bullock
*Assistant Examiner* — Sharon Pregler

(57) ABSTRACT

A selective hydrogenation process that is particularly effective in selectively hydrogenating alkynl compounds, such as acetylene or methyl acetylene, over alkenyl compounds, such as ethylene, is described. The process utilizes a slurry conversion unit for heat efficiency purposes during the conversion of acetylene into ethylene.

22 Claims, 5 Drawing Sheets

SELECTIVE HYDROGENATION OF ALKYNYL-CONTAINING COMPOUNDS AND POLYUNSATURATED COMPOUNDS

PRIORITY

This application claims priority to Provisional Application No. 61/527,367 (2011EM232) filed on Aug. 25, 2011 and EP Application No. 11184559.0 filed on Oct. 10, 2011, the disclosures of which are incorporated herein by reference in their entireties.

FIELD

The present techniques relate to a selective hydrogenation process that is particularly effective in selectively hydrogenating alkynl compounds, such as acetylene or methyl acetylene, over alkenyl compounds, such as ethylene. More specifically, the present techniques relate to a process that utilizes slurry conversion for heat efficiency purposes during the conversion of acetylene into ethylene.

BACKGROUND

Light olefin products (e.g. ethylene, propylene, and butene) may be generated by various technologies, such as gas to olefins, methanol to olefins, steam cracking, pyrolysis or fluid catalytic cracking. These products contain highly unsaturated byproducts, such as alkynes and alkadienes. These byproducts are subsequently removed from light olefins because they can be poisons to downstream processes, such as olefin polymerization catalysts.

One process for removing unsaturated byproducts, such as alkynes and alkadienes, from light olefin streams is selective hydrogenation. Alkynes include acetylene and/or methyl acetylene, while alkadienes include propadiene and/or butadiene. The selective hydrogenation has been carried out using a variety of catalysts. Examples of selective hydrogenation catalysts (e.g., catalytic particles) include nickel or palladium and mixtures thereof supported on alumina.

To perform the selective hydrogenation, four unit types are typically used: (i) front-end selective catalytic hydrogenation converters, (ii) back-end selective catalytic hydrogenation converters, (iii) methyl acetylene/propadiene (MAPD) selective catalytic hydrogenation converters and (iv) butadiene (BD) selective catalytic hydrogenation converters. These converters typically involve different feeds based on the specific process.

Typical acetylene conversion processes utilize fixed bed tubular converters incorporating engineered catalyst structures to manage heat and mass transfer within the converter. The engineered catalyst particles may be impregnated or coated with active catalyst to convert feeds (e.g., acetylene) into products (e.g., ethylene). These processes are generally utilized with lower temperature pyrolysis processes, such as steam cracking, which produce ethylene along with other lower amounts of byproducts, such as acetylene. As an example, the acetylene processed in a steam cracking process is typically less than (<) 2 mole percent (mol %) on feed.

With higher acetylene concentrations, U.S. Pat. No. 4,705,906 describes a process that utilizes greater than (>) 1 mol % carbon monoxide in its process. The catalyst comprises a metal oxide, sulfide, mixture of metal oxides, or sulfides having hydrogenation activity, for example ZnO either alone or in combination with other metal oxides or sulfides. As other examples, U.S. Pat. No. 7,153,807 discloses a selective hydrogenation process that uses non-palladium catalyst as the selective hydrogenation catalyst, while U.S. Pat. No. 7,404,936 discloses the use of microchannel converters.

However, these processes suffer from several limitations. For instance, as the process involves exothermic reactions, the process may lose control of the reactions if the temperature within the unit is not properly managed. For streams with low levels of acetylene (e.g., <2 mol %), the reactions may be managed selectively using conventional techniques because of the lower catalyst activity or heat release rates. However, for streams containing higher levels of acetylene (e.g., ≥2 mol %), conventional processes have problems controlling the reaction temperatures and still remaining highly selective. In addition, the conventional processes are limited by heat and/or mass transfer, as only a small part of the converter volume is used by the active catalyst, and the catalyst has to be configured with low metal loadings and catalytic activity. That is, as the process does not efficiently remove heat, the process has to limit reactions to prevent overheating of the unit. As such, the conventional processes are limited by heat generation and fail to effectively recover energy released in the process.

Further, the production of significant amounts of undesirable compounds, such as saturates (e.g., ethane, propane, butane), as well as the production of green oil ($C_4^+$ oligomer compounds), are problematic with the higher acetylene concentration containing feeds. These saturates are typically formed due to over-hydrogenation of the alkynes and/or alkadienes and the non-selective hydrogenation of olefins. Additionally, green oil is generally formed as a result of oligomerization of the alkynes and/or alkadienes and/or olefins. Both saturates and green-oil are undesirable due to a loss of the desired mono-olefins component of the product stream along with incremental hydrogen consumption. Green oil is additionally troublesome in that it further decreases catalyst life by depositing heavy compounds on the catalyst surface.

As yet another problem, the selectivity is typically modest for vapor phase processes with a portion of the acetylene and/or ethylene converting to ethane and/or other undesired products. This low selectivity may not be problematic for lower temperature conversion processes (e.g., steam cracking), which involves streams having a relatively low acetylene content. However, for higher acetylene content streams, the lower selectivity results in recycles and/or multiple conversion stages. These inefficiencies increase cost of equipment and operations and add unnecessary complexity to the system. To address this concern, some processes may involve absorption to enhance selectivity, such as U.S. Pat. No. 7,692,051. While these processes may enhance the selectivity, they tend to be less energy efficient.

Accordingly, enhancements in selective hydrogenation processes are desired to increase the hydrogenation of alkynyl-containing compounds and/or polyunsaturated compounds over hydrogenation of mono-unsaturated compounds. Additional enhancements in selective hydrogenation processes are also desired, such as increasing heat recovery of the reaction process and increasing feed conversion rate relative to converter volume.

SUMMARY OF THE INVENTION

To overcome at least some of the difficulties encountered during the use of conventional alkynyl (e.g., acetylene) conversion, the present techniques utilize one or more slurry conversion units. Unlike the conventional slurry processes, e.g., Fischer-Tropsch, the slurry conversion unit of the present techniques utilizes a catalyst that is effective for the selective conversion of alkynyls to alkenyls. Beneficially, the selective hydrogenation process of the present techniques can be operated at temperatures enabling efficient heat recovery. For instance, this recovered heat may be integrated to preheat the feed to one or more reactors, heat a utility fluid for use as a diluent, and/or for other processes that enhance the efficiency of the system. Also, the present techniques benefit from the enhanced selectivity via the use of liquid phase slurry over conventional vapor phase processes. Further still, the process may be performed at relatively low pressure as compared to typical conventional acetylene converters, which may reduce compression costs.

According to one aspect of the present techniques, a method of acetylene conversion. The method comprises combining acetylene, molecular hydrogen, carrier fluid and catalytic particles to produce slurry in a slurry conversion unit; exposing the slurry to operating conditions that include an average hydrogenation reaction temperature greater than or equal to 125° C. to produce a vapor product comprising ethylene; and extracting heat from the slurry conversion unit via indirect heat exchange with a utility fluid.

In yet another embodiment, the method may involve processing hydrocarbons to produce ethylene. The method may include combining (i) a first converter feed containing acetylene and molecular hydrogen with (ii) a second converter feed comprising a carrier fluid and catalytic particles to produce slurry in the slurry conversion unit; reacting the acetylene with the molecular hydrogen in the presence of the catalytic particles in the slurry at operating conditions that include an average hydrogenation reaction temperature greater than 125° C. to produce a vapor product comprising ethylene; and extracting heat from the slurry conversion unit via indirect heat exchange with a utility fluid.

In another embodiment, a system for processing hydrocarbons to produce ethylene is described. The system includes a slurry conversion unit and a solvent regeneration unit. The slurry conversion unit is configured to convert a first converter feed into ethylene and has a housing forming an interior region; an inlet medium, an inlet means configured to pass a first converter feed from a location external to the housing to the first interior region, an outlet means configured to pass vapor products from the second interior region to a location external to the housing, a solvent removal means configured to remove at least a portion of the slurry from the second interior region to a location external to the housing, and a solvent injection means configured to pass a solvent into the second interior region. The inlet medium is configured to divide the interior region within the housing into a first interior region and a second interior region; restrict flow of a second converter feed from the second interior region into the first interior region; and permit the flow of the first converter feed from the first interior region into the second interior region. The solvent regeneration unit is in fluid communication with the second interior region of the slurry conversion unit and configured to receive slurry from the second interior region from the solvent removal means; separate solvent from contaminates in the slurry; and pass the decontaminated solvent to the solvent injection means.

In still yet another embodiment, a method for processing hydrocarbons to produce ethylene is described. The method comprises exposing a first pyrolysis feed to a peak pyrolysis gas temperature≥1500.0° C. within a first conversion reactor to produce a first reactor effluent; exposing a second pyrolysis feed to a peak pyrolysis gas temperature≥700.0° C. within a second conversion reactor to produce a second reactor effluent; combining the first reactor effluent with the second reactor effluent to produce a combined reactor effluent; combining acetylene, hydrogen, carrier fluid and catalytic particles to produce a slurry in a slurry conversion unit, wherein the acetylene is derived from the combined reactor effluent; and exposing the slurry to an average hydrogenation reaction temperature greater than or equal to 125° C. to produce a vapor product comprising ethylene.

In another embodiment, an acetylene conversion method is described. The method comprises combining acetylene, hydrogen, solvent and catalytic particles to produce a slurry in a slurry conversion unit, wherein the solvent is selective to absorb acetylene as compared to absorbing ethylene; exposing the slurry to an average hydrogenation reaction temperature greater than or equal to 125° C. to produce a vapor product comprising ethylene; and extracting heat from the slurry conversion unit via indirect heat exchange with a utility fluid. In yet another embodiment, the method comprises: exposing a pyrolysis feed to a peak pyrolysis gas temperature≥1500.0° C. within a conversion reactor to produce a reactor effluent; adjusting an ethylene to acetylene mole ratio of the reactor effluent to have an ethylene to acetylene mole ratio less than or equal to 2:1, 5:1 or 10:1; passing the adjusted reactor effluent to a slurry conversion unit; and producing ethylene from hydrogenation of the adjusted reactor effluent.

In one or more of these embodiments, the feeds and products may be utilized to enhance the process. For instance, the first converter feed may include at least 2 mol % acetylene based on the total first converter feed. Also, the catalyst particles may convert alkyne to alkene at operating conditions sufficient to yield a conversion rate of at least 0.4 moles/hour/cc of catalytic particles, or of at least 2 moles/hour/cc of catalytic particles.

In one or more other embodiments, the process may utilize the recovered heat to further enhance the process. For instance, at least a portion of the recovered heat may be utilized to perform one or more of (i) generating steam from the heated utility fluid, (ii) converting the heated utility fluid into energy utilized within the process, (iii) combining the heated utility fluid with a pyrolysis feed provided to a conversion reactor upstream of the slurry conversion unit, and (iv) heating a pyrolysis feed via the heated utility fluid. Also, at least a portion of the recovered heat may be utilized reduce one or more feeds (e.g., reactants and/or pyrolysis feed) utilized in a conversion reactor upstream of the slurry conversion unit. This heat may be recovered by passing the utility fluid through a bank of heat exchange tubes within the slurry conversion unit to extract the heat. The utility fluid may be one or more of water and steam.

Figure 1:
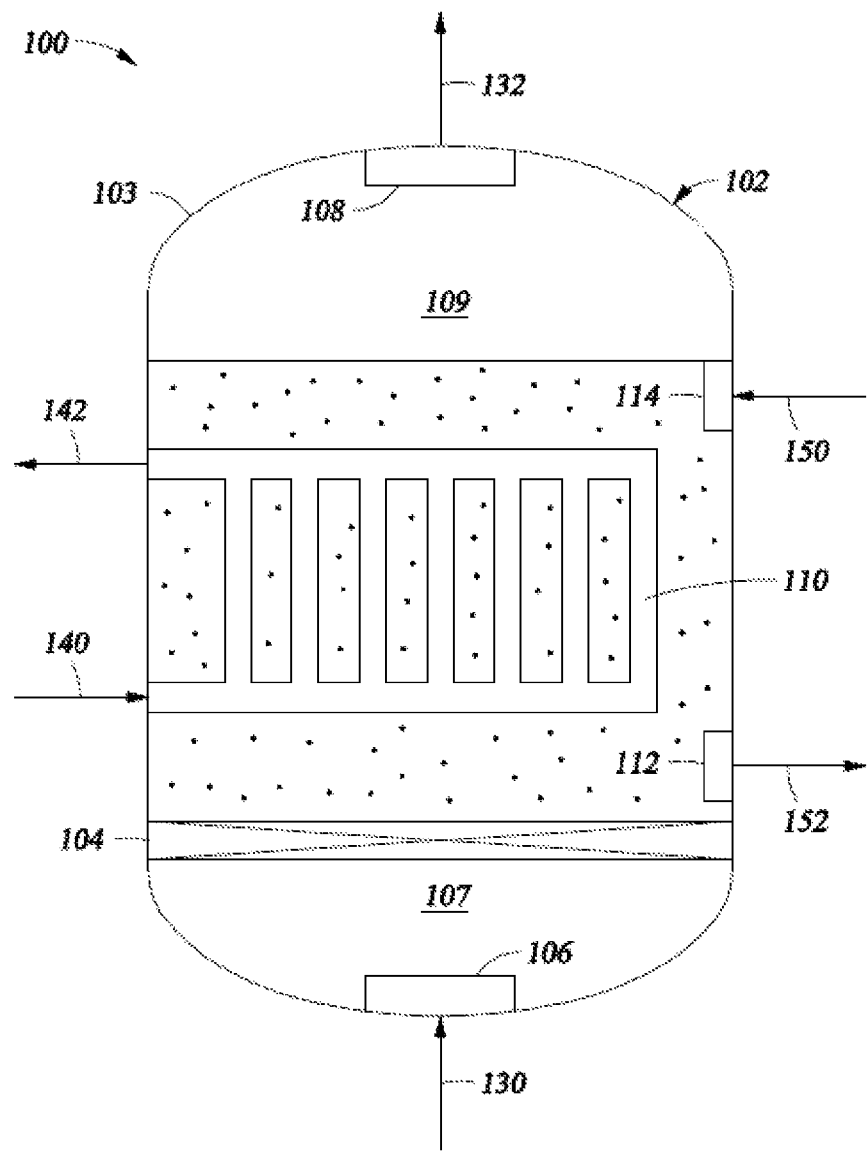
FIG. 1 is a simplified diagrammatic illustration of an exemplary slurry conversion unit in accordance with an embodiment of the present techniques.

Although the invention is described in terms of a conversion process for producing ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION

I. Selectively Hydrogenating Acetylene

The present techniques provide an enhanced process for selectively hydrogenating alkynyl compounds in a slurry conversion unit. Selective hydrogenation in the present techniques refers to the hydrogenation of alkynyl compounds (e.g., acetylene) to produce alkenyl compounds (e.g., ethylene), such that the process has an increased amount of alkenyl compounds as compared to the initial feed provided to the process. The process is particularly effective in the selective hydrogenation of acetylene to produce predominantly ethylene from the converted acetylene. Although some alkyl compounds may be formed, such as ethane, selective hydrogenation favors the formation of alkenyl compounds.

Unlike conventional acetylene conversion processes, the present techniques utilize a slurry conversion unit to produce ethylene from the reactions of acetylene, hydrogen, carrier fluid (e.g., a solvent) and catalyst particles. This process may involve mixing a first converter feed containing acetylene and hydrogen with a second converter feed containing a carrier fluid (e.g., solvent) and catalyst particles. Based on this process, the present techniques provide various enhancements as compared to conventional acetylene processes. For instance, the process may utilize high velocity turbulent slurry bubble columns along with high activity catalyst material, which are not typically utilized due to heat and/or mass balance transfer limitations in typical acetylene conversion systems. These limitations may involve the inability of the acetylene converter to efficiently remove the heat produced from the exothermic reactions, which results in overheating of the catalyst within the converter. This overheating may be problematic in a fixed bed or continuous process, which does not properly manage heat removal from the reactions. As a result, low activity catalysts are typically utilized in these processes, which include fixed bed acetylene converters. Accordingly, the slurry conversion unit provides higher volumetric productivity and higher catalyst utilization as compared to typical fixed bed acetylene conversion units. For example, conventional acetylene conversion processes may utilize catalyst material having a loading of <0.1 wt % active metal deposited within the tubular converters. By contrast, the present techniques may utilize small particles having active catalyst material (e.g., palladium) disposed on a support structure (e.g., alumina) with loadings ≥1 wt % of the particles. In addition, the carrier fluid may be a solvent, which is utilized to dissolve certain byproducts, such as those formed by oligimerization of acetylene into polyacetylene (e.g., green oil). This prevents certain byproducts from coating or being deposited on the catalyst particles.

Further, the present techniques provide energy efficiencies by recovering at least a portion of the heat released during the hydrogenation reactions, which may be utilized for other purposes. In an embodiment, a particularly efficient means of capturing the heat is through the production of steam via different tube banks within the slurry conversion unit. As an example, the process may involve average hydrogenation reaction temperatures greater than or equal to (≥) 200° C., ≥250° C., or ≥275° C. and less than or equal to (≤) 400° C., ≤450° C. or ≤500° C. within the slurry conversion unit, which may produce steam at a pressure of at least 100 psig (689 kPa) and/or at least 200 psig (1379 kPa). The steam can be used for various purposes, such as the working fluid for steam turbine machinery and/or compressors, as a co-feed into catalytic conversion processes, and/or as a diluent and/or heat transfer medium into thermal cracking processes.

Moreover, the present techniques provide enhanced processing because active catalytic materials may be utilized to enhance conversion and selectivity. While conventional techniques may utilize multiple acetylene conversion units due to the lower selectivity, the present techniques may utilize more active catalyst because the heat produced may be removed and/or recovered from the slurry conversion unit. Accordingly, the enhanced efficiency for the process may further reduce equipment costs and complexity, while providing energy recovery. This recovered energy may be utilized within the process for further efficiency enhancements.

Further still, the process provides flexibility and scalability. That is, the slurry conversion unit is able to scale to handle higher volumes of acetylene, which may be utilized to provide large scale hydrogenation of acetylene in high temperature conversion processes. Unlike conventional acetylene converters that are limited in size by the heat transfer rate and mass transfer rate (e.g., rate of reaction versus pore diffusion with the catalyst particles), the slurry conversion unit is scalable to a variety of sizes by lessening such limitations. As a result, the slurry conversion unit may be adjusted in size and/or catalytic activity for different configurations, without the need for additional units.

In one or more embodiments, particular hydrocarbons useful according to the present techniques are those that can be pyrolyzed to produce a product containing alkenyl containing compounds, alkynyl containing compounds or both. Particularly preferred are hydrocarbon compounds that can be pyrolyzed to produce an effluent containing ≥1 mol %, more preferably ≥3 mol %, and most preferably ≥6 mol % alkynyl containing compounds, based on total moles of effluent produced from the pyrolysis process. The preferred alkynyl containing product comprises acetylene. As an example, the first converter feed may be derived from the products of a reactor, which may operate by exposing a pyrolysis feed to temperatures≥1200° C., ≥1500° C., or even ≥1600° C. The hydrocarbon feed or pyrolysis feed to the reactor may include, by way of non-limiting examples, one or more of methane, natural gas, naphtha, ethane, mixtures or components thereof, or other hydrocarbon feeds as noted in U.S. Patent Application Ser. Nos. 61/434,417 and/or 61/434,409, which are each hereby incorporated by reference in their entirety.

II. Converter Feeds

The converter feeds may include a mixture of alkynes (e.g., acetylene), hydrogen, carbon monoxide, carrier fluid (e.g., solvent), and catalytic particles, along with or without other components (e.g., ethylene and the like). The converter feeds may be provided in any suitable manner to the slurry conversion unit. For instance, the streams may be provided individually and/or may be provided together in different combinations. For instance, the solvent may be mixed with the acetylene and hydrogen prior to the slurry conversion unit and/or the solvent may be provided with the catalytic particles in the slurry conversion unit.

In one embodiment, the converter feeds may be provided as a first converter feed containing acetylene and hydrogen and a second converter feed containing solvent and catalytic particles. The first converter feed (e.g., feed stream that includes the alkyne to be selectively hydrogenated) can come from any suitable source. The first converter feed includes a sufficient amount of alkyne to produce heat that can be recovered for energy efficiency purposes. Preferably, the first converter feed includes alkyne in an amount of $\geq 2$ mol %, $\geq 5$ mol %, $\geq 10$ mol %, or $\geq 20$ mol %, the content of the alkyne being based on total mole of the first converter feed. The alkyne content being less than the auto-detonation limit for given operating conditions. Preferably, the alkyne is acetylene and/or methyl acetylene, more preferably acetylene. The first converter feed can include non-alkyne compounds. Preferably, the first converter feed includes $\leq 98$ mol % non-alkyne compounds, alternatively $\leq 90$ mol % non-alkyne compounds, alternatively $\leq 80$ mol % non-alkyne compounds, alternatively $\leq 70$ mol % non-alkyne compounds, the content of the non-alkyne compounds being based on total mole of the first converter feed.

The second converter feed may contain catalyst particles and a carrier fluid, such as a solvent. The carrier fluid, which may preferably be a solvent, may be utilized to balance several properties, such as volatility, viscosity and solvency (reactants and/or certain products) at process conditions (e.g., at steady-state operating conditions or operating conditions), while the catalyst particles may include varying amounts of active catalytic materials.

The volatility of carrier fluid (e.g., solvent) is preferred to be low. This property may be selected to lessen the amount of slurry that vaporizes within the slurry conversion unit. Further, if a solvent is utilized as the carrier fluid, the lower volatile solvents may reduce the amount of solvent that has to be added to the system (e.g., reduce solvent make-up), which may lower operating costs. In an embodiment, the solvents may have a boiling point at 1 atmosphere of $\geq 125°$ C., $\geq 150°$ C., or $\geq 200°$ C., but may be $\leq 400°$ C. If the carrier fluid comprises a mixture of compounds, higher boiling point fluids may be utilized, with the boiling point in mixtures referring to final boiling point as determined by testing method ASTM D 86.

The viscosity may be configured to optimize the mixing of gas and/or liquid with the catalytic particles within the slurry. The viscosity may be selected to lessen the tendency of catalytic particles to settle and optimize the distribution of catalytic particles within the slurry. As a viscosity related characteristic, the mass transfer characteristics of the carrier fluid may facilitate the stabilization of small bubbles in the slurry, the exchange of reactant gases into the catalyst particles, and the removal of ethylene into vapor phase from the slurry. Further, the certain carrier fluids (e.g., solvents) may lessen the hydrogenation of alkenes (e.g., ethylene into ethane).

The carrier fluid may also be selected based on its ability to dissolve, disperse or absorb certain compounds. For instance, if the carrier fluid is a solvent, the solvent may be selected to dissolve, disperse, or absorb reactants (e.g., acetylene and hydrogen) and certain products (e.g., green oil). Further, the solvent may also be selected to release ethylene from the liquid phase (e.g., selectively deabsorb the ethylene from a liquid phase into a gas phase) to avoid over conversion of the ethylene into ethane.

In one embodiment, the carrier fluid may be a solvent that is selected to absorb acetylene, but not ethylene. That is, the solvent may selectively absorb acetylene into the liquid phase at a higher selectivity as compared to ethylene, while the ethylene may primarily remain in the vapor phase. For example, NMP has a greater than 20:1 selectivity to acetylene relative to ethylene. In this manner, the ethylene may remain a non-preferred path as compared to acetylene in the slurry. This may assist in the removal of ethylene from the slurry and lessen over hydrogenation of the ethylene into ethane or other non desired products. Examples of such solvents may include di-methyl formamide (DMF) tetrahydrofuran (THF), N-methylpyrrolidone (NMP) or other suitable solvent compounds.

The carrier fluid may also include solvents that are slightly to moderately polar. Preferred solvents are fluids that solubilize green oil. Such fluids are preferably polar aprotic fluids and steam. Polar fluids are those that have a large dipole moment, high dielectric constant, aromatic ring structures, or a combination thereof. Typical solvents include diphenyl ether, furfurol, N-alkyl pyrrolidones, dimethyl carbonate, carbonate derivatives of higher hydrocarbons, ethylene glycol, diethylene glycol, triethylene glycol, ethoxylates, norpar and isopar solvents, acetone, oxo alcohols, and heavier high purity paraffins, which are a liquid at operating conditions in the slurry conversion unit.

In an embodiment, the solvent has a dipole moment of at least 0.1 debye (D), preferably at least 1.6 D, and more preferably at least 2.8 D. Dipole moments for a solvent may be found in the *CRC Handbook of Chemistry and Physics* (65th ed.), CRC Press, or may be determined by measuring the capacitance with a dipole meter. The preferred dipole moment may be in the range from 2.0 D to 4.0 D. Each of the measurements indicated are measurements under standard temperature and pressure conditions, e.g., 20° C. and 1 atmosphere.

The solvent can be a polar aprotic fluid. The aprotic fluids are fluids that have a relative static permittivity greater than 15. Protic fluids refer to compounds that have a hydrogen atom bound to an oxygen (as in a hydroxyl group) or a nitrogen (as in an amine group) atom. More generally, any compound that contains dissociable proton(s) ($H^+$), or that can donate a proton ($H^+$), is referred to as a protic fluid. Conversely, aprotic fluids cannot donate hydrogen. Aprotic fluids refer to compounds that do not contain dissociable proton(s) ($H^+$), or that do not donate a proton ($H^+$), but have a large dipole moment, such as at least 1.5 D. In one aspect, this large dipole moment is generated by bonds between carbon and either oxygen or nitrogen. Examples of aprotic fluids include, but are not limited to, dichloromethane, tetrahydrofuran, ethyl acetate, acetone, dimethylformamide, acetonitrile, and dimethyl sulfoxide.

The carrier fluid (e.g., solvent) may include a mixture of different compounds. In such a mixture, every compound in the mixture may not individually meet the desired characteristics of polarity, such as dipole moment, and dielectric constant. However, if the carrier fluid is comprised of a mixture of compounds, the overall mixture should exhibit the desired polarity characteristics. For example, the mixture of components should exhibit the desired characteristics of one or more desired dipole moment, and dielectric constant.

The catalyst particles may include a catalytic material and may optionally include a support structure. The catalytic material's composition (catalyst composition) used according to the present techniques is capable of hydrogenating alkynes. Examples of such alkynes include $C_2$ to $C_4$ alkynes, such as acetylenic compounds (e.g., acetylene and methyl acetylene). The alkynes can be included in a first converter feed that also contains other compounds, such as olefins, and in such a case, the catalyst has high selectivity to produce olefins and low selectivity to produce green oil (oligomers formed from two or more alkyne or olefin molecules) and saturates. In particular, when used to selectively hydrogenate one or more of $C_2$ to $C_4$ alkynes in a feed that may also contain one or more of $C_2$ to $C_4$ olefins, the selective hydrogenation catalyst (e.g., catalytic particles) can achieve an alkyne conversion in excess of 80 mol %, such as in excess of 90 mol %, with a selectivity to olefin based on alkynes converted in excess of 50 mol %, such as in excess of 60 mol % or in excess of 70 mol %, and a green oil selectivity of less than 10 wt %, such as less than 8 wt % or less than 4 wt %. The reduction in green oil formation should also result in an extension of catalyst lifetime and/or operating cycle.

The selectivity ratio may be defined as a molar ratio of alkenes to converted alkynes for the process. For instance, the acetylene selectivity is the molar ratio of the acetylene converted to ethylene over the total amount of acetylene converted. If this ratio is below 0.5, then the catalytic material has low selectivity. For selectivity ratios≥0.5, the catalytic material has high selectivity. Accordingly, in certain embodiments, the high selectivity includes a selectivity ratio≥0.5, ≥0.6, or ≥0.8.

The catalyst composition may contain at least one metal from Groups 8 to 10 of the Periodic Table of the Elements. The Periodic Table of Elements referred to herein is the IUPAC version described in the *CRC Handbook of Chemistry and Physics,* 78th Edition, CRC Press, Boca Raton, Fla. (1997). Examples of metals from Group 8 include iron, ruthenium and osmium, with iron and ruthenium being preferred metals. Examples of metals from Group 9 include cobalt, rhodium and iridium, with rhodium being a preferred metal. Examples of metals from Group 10 include nickel, palladium and platinum, with palladium and platinum being preferred metals, and palladium being more preferred. In one or more embodiments, the catalytic particles may include greater than (>) 0.5 wt % palladium or platinum based on the weight of the catalyst particle.

In certain embodiments, the catalyst composition contains a quantity of elements from at least one of the Groups 8 to 10 metals to convert alkyne to alkene at operating conditions sufficient to yield a conversion rate of at least 0.1 moles/hour/cc catalytic particles or hydrogenation catalyst. Preferably, the catalyst composition contains a quantity of elements from at least one of the Groups 8 to 10 metals to convert alkyne to alkene at operating conditions sufficient to yield a conversion rate of at least 0.4 moles/hour/cubic centimeter (cc) of catalytic particles, alternatively at least 2 moles/hour/cc of catalytic particles, alternatively at least 5 moles/hour/cc of catalytic particles. Generally, the catalyst composition should contain a quantity of at least one of the Groups 8 to 10 metals to convert alkyne to alkene at operating conditions sufficient to yield a conversion rate of up to and including 10 moles/hour/cc of catalytic particles (e.g., ≤10 moles/hour/cc of catalytic particles).

In an embodiment, the catalyst particle comprises at least 0.3 weight percent (wt %) Groups 8 to 10 metals, based on total catalytic particle composition. The catalytic material can comprise at least 1 wt %, at least 2 wt %, at least 4 wt %, or at least 5 wt % Groups 8 to 10 metals, based on total catalytic particle composition. Generally, the catalytic particle's composition contains up to and including 10 wt % Groups 8 to 10 metals based on the total catalytic particle's composition.

The catalyst composition may aid in the selective hydrogenation reactions that produce sufficient heat, such that at least a portion of that heat can be recovered for energy efficiency purposes. For example, the recovered heat may be utilized to generate steam that can be used as a heat source. According to the present techniques, the catalyst composition aids in the recovery of heat by having the ability to release heat produced in the selective hydrogenation reaction. Preferably, the heat produced in the hydrogenation reaction is produced at operating conditions sufficient to yield a catalyst heat release rate of at least 0.5 Mega Joules/hour/cubic centimeter (MJ/hr/cc) of hydrogenation catalyst or catalytic particles. Alternatively, the heat produced in the hydrogenation reaction is produced at operating conditions sufficient to yield a catalyst heat release rate of at least 2 MJ/hr/cc of catalytic particles or at least 10 MJ/hr/cc of catalytic particles. Generally, the heat produced in the hydrogenation reaction should be produced at operating conditions sufficient to yield a catalyst heat release rate of up to and including 40 MJ/hr/cc of catalytic particles (e.g., ≤40 MJ/hr/cc of catalytic particles).

In addition to the one or more metal components discussed above, the catalytic particle composition may include a support structure, which may include a solid oxide or other refractory material along with binder material. Suitable support structure materials include, but are not limited to, carbon, silicon nitride, silicon carbide, boron nitride, magnesium silicate, bentonite, zeolites, metal alloys, zirconia, alumina, silica, silica-alumina, ceria-alumina, aluminates (such as aluminates of Groups 1 and 2 of the Periodic Table of Elements), and magnesium oxide-silicon oxide mixtures. Supports structures are typically non acidic or low acidity to minimize green oil formation. Preferred support structure materials include carbon, zirconia, alumina, silicas, and ceria-alumina. The support structure material can comprise from 80 wt % to 99 wt %, alternatively from 80 wt % to 95 wt % of the entire catalytic particle composition, while the catalytic material may have a loading of up to the remaining weight percent. For example, the catalytic material may be from 0.3 wt % to 10 wt %, alternatively from 2 wt % to 5 wt % of the entire particle composition.

The catalyst may also contain other promoters or modifiers that are used to further improve selectivity for selective alkyne hydrogenations. Examples include Group 11 to 14 elements, such as copper, silver, zinc, tin, and gallium and/or alkali or alkali earth additives from Groups 1 and 2. In a preferred embodiment, the additional components or promoters are used to improve activity or selectivity for selective hydrogenation of alkynes to alkenes as compared to the unmodified catalyst. Alternative modifiers include other Group 11 to 14 elements, such as gold or indium, alone or in combination, or in combination together with one or more alkali or alkali earth additives such as potassium, magnesium, calcium, etc. The catalyst may comprise about 0.1 wt % or more of modifier or promoter element, and, generally, the atomic ratio of promoter elements to Group 11 to 14 metals that are in the range of about 0.1 to 5, although lower or higher ratios can be utilized depending on specific cost and performance tradeoffs. These various combinations of promoters may include two, three or more different modifiers.

The catalyst material may be disposed on support structures to form particles of various different shapes and/or sizes. For instance, the particles may include spherical objects, elliptical objects, and/or irregular shaped objects. The catalytic material may be disposed via spraying or other suitable techniques. For instance, the outer surface of the support structure that forms an internal region isolated from the external conditions may have catalytic material disposed on the outer surface opposite the internal region or the support structure having orifices through the object may have catalytic material disposed on specific surfaces and/or over each of the surfaces. These particles may also be varied in size. For example, the particles have an average diameter≥0.1 micrometer (μm), ≥1.0 μm, ≥10 μm, or ≥40 μm, but ≤500 μm, ≤250 μm, ≤150 μm, or even ≤100 μm.

The loading of catalyst particles within the slurry can be varied over a wide range depending on catalyst activity and target rates for converting acetylene to ethylene. In some embodiments, the slurry has solid loadings of 2 wt % or 5 wt % to 40 wt %, preferably about 15 wt % to 30 wt %, or more preferably about 20 wt % to 25 wt %. That is, the steady state slurry may include catalytic particles in the range of 5 wt % to 40 wt %, in the range of 15 wt % to 30 wt %, or in the range of 20 wt % to 25 wt % based on the weight of the slurry.

The converter feed may also contain small levels of additional additives, such as carbon oxides, especially carbon monoxide. Depending on the specific catalyst and operating conditions, addition of carbon monoxide into the converter feed can be used to reduce formation of fully saturated hydrocarbons such as ethane. Carbon oxides are typically used at lower concentrations in the range of 0.1 to 5 mol % based on the feed gas mixture entering the selective hydrogenation unit. Additionally, other additives may include triphenylphosphine (TPP), as an example.

III. Slurry Conversion Unit and Process Conditions

The slurry conversion unit and process conditions may be utilized to selectively hydrogenate the first converter feed (e.g., alkyne-containing feed stream) by flowing a first converter feed through the second converter feed containing the solvent and the catalytic particles in the slurry conversion unit. As the first converter feed flows through the slurry conversion unit, catalyst within the conduit acts to convert alkyne to alkene products and to produce heat. Accordingly, the slurry conversion unit may include various components to recover heat from the reactions and manage the byproducts formed from the reactions. As an example, the slurry conversion unit may include a housing, an inlet means, a bank of heat exchange tubes, and an outlet means. Optionally, the slurry conversion unit may also include an inlet medium, circulation means, slurry regeneration means, and/or catalytic particles and/or solvent regeneration means, etc.

The slurry conversion unit may include any of a variety of components and configurations. As noted in U.S. Pat. Nos. 5,157,054; 5,382,748; 5,911,468; 5,866,621; and 5,962,537, different exemplary slurry units for different processes are described, which are each incorporated by reference. While these units are utilized for Fischer Tropsch processes, certain aspects may be utilized in the present techniques. That is, certain features may be utilized to convert acetylene in gas mixtures containing relatively high acetylene levels (e.g., ≥2 mole %, ≥20 mole %, or even >40 mole % in the first converter feed).

The housing provides one or more internal region(s) within the slurry conversion unit that are separated from external locations. The housing may include an inner shell surrounded by an outer shell with insulation disposed in between. Certain surfaces of the housing (e.g., the inner surface and outer surface) are preferably made of a hard material, such as a ceramic, an iron based alloy such as steel, or monel. More preferably, the surfaces are comprised of stainless steel or inconel or other alloy, which is durable (capable of withstanding temperatures of the process conditions while supporting the pressures of the process conditions within the slurry conversion unit).

The housing can be of any suitable shape. In an embodiment, the housing may have a cross section in the form an oval, including a circle, or in the form of any typical multi-sided geometric form, such as in the form of a rectangle, including a square. Also, the housing may have a cross sectional area of at least 2 $m^2$, at least 10 $m^2$, at least 40 $m^2$, or at least 150 $m^2$. The height of the housing may be greater than 2 m, greater than 10 m, greater than 20 m, or greater than 60 m. The cross sectional area as referred to herein is measured on the basis of the area of the housing open to fluid flow and excluding surfaces and insulation.

The inlet means is configured to receive the one or more feed streams (e.g., the first converter feed), which may be a vapor and/or liquid phase streams, from a location external to the housing's internal region and pass the feed stream into a portion of the internal region. This inlet means may include a sparger, contactor, gas distributor tray, multiple nozzles or injectors arranged on a distributor tray, or other suitable equipment.

The outlet means is configured to pass the conversion products, which may be a vapor and/or liquid phase streams, to a location external to the housing's internal region from the internal region. Product removal is accomplished by removing overhead vapor and any liquid product, if any, through filter systems which may recycle any solvent and catalytic particles back to the slurry conversion unit. The liquid product recovery may include depressurizing the liquid product to recover dissolved gases which are vaporized and then separated using traditional methods for olefin recovery. Vaporization and release of dissolved gases from the liquid phase may be enhanced by heating or partial fractionations. The solvent and/or catalytic particles are then recirculated back to the slurry conversion unit and/or combined with fresh feed and reintroduced into the unit. The outlet means may include filters, separators, valves and/or conduits.

The bank of heat exchanger tubes should have tubular and cross sectional areas that provide for effective heat transport of heat produced during the selective hydrogen process. The effective transport of heat means that heat produced can be efficiently transported through the heat exchange tubes so that at least a portion of the heat can be recovered for reuse. Preferably, the heat is recovered in the form of steam. The bank of heat exchanger tubes may include a plurality of conduits disposed within the housing and in fluid communication with locations external to the housing. The plurality of conduits may contain, for example, 2, 10, 100, 1000 or more conduits. In some preferred embodiments, a plurality of conduits is arranged in parallel arrays of planar conduits.

Further, the heat exchange conduit can have different cross sectional profiles to affect the heat exchange. For instance, the heat exchange conduit may have a cross section in the form an oval, including a circle, or in the form of any typical multi-sided geometric form, such as in the form of a rectangle, a hexagon, a square, an octagon and the like. In addition, the heat exchanger conduit may include fins or other irregular surface areas on at least a portion of the interior surfaces of the conduit and/or on at least a portion of the exterior surfaces of the conduit.

During operation, the heat exchange conduits contain a utility fluid (e.g., water and/or steam) that is flowed through the conduits. The flow of the utility fluid may be co-flow, counter-flow, cross-flow or a combination of flows (diagonal flow) relative to the flow of the mixtures within the housing (e.g., flow of the first converter feed into the second converter feed). Performance advantages in the use of this type of converter architecture for the purposes of the present techniques include relatively large heat and mass transfer rates, substantial reduction or absence of any explosive limits, and provide a relatively isothermal profile.

In some embodiments, the heat exchange conduit contains a "bulk flow region" or an open flow path. The terms "open flow path" or "bulk flow region" refer to an unobstructed, contiguous bulk flow region within the conduit. A contiguous bulk flow region allows rapid flow through the conduit without large pressure drops. In preferred embodiments, there is laminar flow in the bulk flow region. Bulk flow regions within each conduit preferably have a cross-sectional area of $5 \times 10^{-8}$ to $1 \times 10^{-2}$ $m^2$, more preferably $5 \times 10^{-5}$ to $1 \times 10^{-3}$ $m^2$. The bulk flow regions preferably comprise at least 5%, more preferably 30-80% of either: 1) the internal volume of the conduits, or 2)

the cross-section of the conduits. Flow patterns as well as flowrate can be tailored to achieve desired temperature gradients within the reaction channels along the flow direction. Utility fluids may include any known heat transfer fluids, such as water, aqueous solutions, silicone oils, molten salts, liquid metals, etc. In some preferred embodiments, the utility fluid is steam or is a fluid that undergoes a phase change in the heat exchange conduits under the intended process temperatures, which may be utilized as noted above.

Optionally, the slurry conversion unit may also include other components, such as an inlet medium, circulation means (e.g., downcomers or circulation conduits and equipment), slurry, solvent and/or catalytic particle regeneration means (e.g., solvent regeneration means, such as removal filters, solvent input means, solvent output means and associated equipment and/or catalytic material regeneration means, such as removal filters, catalytic input means, catalytic output means and associated equipment).

The inlet medium forms a barrier to the slurry (e.g., the solvent and/or particles), while allowing the acetylene and hydrogen to pass through the inlet medium to mix with the slurry. The inlet medium may include a tray with gas or liquid nozzles that is impervious to slurry.

For the circulation means, the slurry conversion unit may include downcomers, circulation conduits, pumps, filters and/or other equipment to distribute the catalytic particles within the slurry in the slurry conversion unit. As an example, downcomers may be utilized to encourage solid circulation and vapor/liquid disengagement. An example of these downcomers may include downcomers in U.S. Pat. No. 5,962,537.

The solvent regeneration means may include one or more solvent removal filters, solvent input means, solvent output means and associated equipment. This may include one or more flash drums, fractionators or other separation units.

The catalytic particle regeneration means may include one or more catalytic particle removal filters, catalytic particle input means, catalytic particle output means and associated equipment. The catalytic particle regeneration means may utilize the electro-magnetic and/or magnetic properties of the catalytic particle to separate the catalyst particles from the slurry if the catalyst particles are magnetic or paramagnetic, as is disclosed in the prior art. The catalyst particles regeneration may include removing the green oil, carbonaceous residues, and/or other impurities from the catalyst particles. This may be performed via oxidation or suitable processes.

The slurry regeneration means may include one or more solvent and/or catalytic particle removal filters, solvent and/or catalytic particle input means, solvent and/or catalytic particle output means and associated equipment, which may be integrated in a variety of configurations to provide the separation based on the solvent and/or catalytic particle utilized.

Suitable process conditions (e.g., operating conditions or steady state operating conditions) of the alkyne hydrogenation process include an average hydrogenation reaction temperature $\geq 125°$ C., $\geq 150°$ C., $\geq 200°$ C., or $\geq 250°$ C. or $\geq 275°$ C., but $\leq 500°$ C., $\leq 450°$ C., $\leq 400°$ C. or $\leq 300°$ C. In certain embodiments, the average reaction temperature may be in the range from 125° C. to 500° C.; alternatively, from 150° C. to 400° C., from 250° C. to 400° C., or 200° C. to 300° C. The average hydrogenation reaction temperature may be measured via thermocouples located within the slurry conversion unit and/or associated with the slurry conversion unit. The average hydrogenation reaction temperature may be the average over a period of time for one or more thermocouples during the slurry conversion unit steady state operation.

The process conditions may also include operating pressures, which include an average reaction pressure of $\geq 4$ psig (27 kPa), $\geq 15$ psig (103 kPa), $\geq 36$ psig (248 kilo Pascal (kPa)), $\geq 44$ psig (303 kPa) or $\geq 103$ psig (710 kPa), but may be $\leq 300$ psig (2068 kPa), $\leq 163$ psig (1124 kPa), or $\leq 150$ psig (1034 kPa). Preferably, the average reaction pressure may be in the range from 15 psig to 500 psig (103 kPa to 3447 kPa); an average reaction pressure of from 50 psig to 500 psig (345 kPa to 3447 kPa); or an average reaction pressure of from 15 psig to 100 psig (103 kPa to 689 kPa).

Hydrogen is also added along with the alkyne in the feed to the converter. Preferably, the feed includes hydrogen at a $H_2/C_2H_2$ molar feed ratio of from 0.5 to 50; alternatively from 1.0 to 20. In various embodiments, feed hydrocarbons can be contacted and mixed with solvent before contacting with hydrogen, the gas streams can be separately fed into the lower section of the converter, or the gas streams can be premixed before contacting with solvent. Combinations for these feed methods can also be utilized.

The slurry conversion unit is preferably operated in the churn turbulent regime to enhance mass and heat transfer. The churn turbulent regime is described in U.S. Pat. No. RE39073, which is incorporated by reference in its entirety. Typically, this means superficial gas velocities above about 10 centimeter/second (cm/sec), or more preferably above about 15 cm/sec. As noted above, the first converter feed may be introduced in the vapor phase or in an absorbed liquid phase. In the vapor phase, the reaction can be carried out at a gas hourly space velocity (GHSV) of from 100 to 25,000 $hr^{-1}$, from 500 to 5,000 $hr^{-1}$, from 10,000 to 25,000 $hr^{-1}$ or from 11,000 to 15,000 $hr^{-1}$ based on the alkyne containing feed gas. In the liquid phase, the reaction can be carried out at an average residence time of 5 seconds to 1 hour, preferably about 0.3 to 10 minutes.

The slurry conversion unit may operate in a fully back-mixed mode. Accordingly, it may be preferred to incorporate one or more baffles and/or other internal flow management devices to reduce the extent of back mixing. Reduction of back mixing can reduce levels of alkyne over hydrogenation to alkanes, especially when the converter is operated at high levels of alkyne conversion.

As an example, FIG. 1 is a simplified diagrammatic illustration of an exemplary configuration 100 of a slurry conversion unit 102 in accordance with an embodiment of the present techniques. The slurry conversion unit 102 includes a housing 103, an inlet means 106, an inlet medium 104, a bank of heat exchange tubes 110, an outlet means 108, a carrier fluid removal means 112 and carrier fluid injection means 114.

In this configuration 100, a second converter feed of catalyst particles are dispersed and suspended in a carrier fluid, such as a solvent. The first converter feed containing acetylene and hydrogen is passed to a first interior region 107 within the housing 103 via line 130 and inlet means 106. The first interior region 107 is isolated from the second interior region 109 that includes the slurry (e.g., second converter feed, first converter feed and reaction products) via the inlet medium 104. If the first converter feed is in the vapor phase, the inlet medium 104 is a suitable gas distribution means arrayed across an otherwise impervious tray disposed between the first and second interior regions. The first converter feed passes through the inlet medium 104 and forms bubbles that intermingle with the second converter feed in the slurry. The slurry exothermically reacts to produce ethylene and heat. The released heat is recovered by the utility fluid passing through the conduits 110. The ethylene and other light gases migrate toward the outlet means 108 within the second interior region, disengage from the slurry and are removed as vapor and/or liquid products via line 132 for further processing.

To recover heat in the slurry conversion unit 102, the utility fluid is provided to the conduits 110 via line 140. The utility fluid, which is not intermingled with the slurry, may pass through one or more of the conduits (e.g., heat exchange tubes) before being removed via line 142 for use in other processes. Accordingly, by the indirect heat exchange, the utility fluid is heated. The utility fluid may be provided to the bank of heat exchange conduits 110 at a nominal temperature of 50° C. to 250° C. and be removed via line 142 at a nominal temperature of 110° C. to 450° C. The bank of heat exchange conduits 110 may optionally be operated at a nominal pressure of about 50 psig up to a pressure of 1000 psig (103 kPa to 6994 kPa).

As the carrier fluid may be contaminated by impurities or byproducts (e.g., green oil) as part of the process, the slurry conversion unit 102 may include a carrier fluid removal means 112 and a carrier fluid injection means 114. The carrier fluid removal means 112 may be a suitable liquid filtering means arranged internal to external to the second interior region, which is impervious to the catalytic particles disposed within the second interior region. The carrier fluid removal means may pass the carrier fluid and other liquid phase components of the slurry through a filter to regeneration equipment. The regeneration equipment (not shown) may include one or more conduits and one or more filtration and fractionation vessels external of the housing 103. Such regeneration equipment may separate contaminates from the carrier fluid and remove contaminates from the process, while recycling the decontaminated carrier fluid back to the carrier fluid injection means 114 for insertion back into the second interior region.

IV. Conversion Reactor as Source for Converter Feed

In certain embodiments, the converter feed containing the alkyne (e.g., first converter feed), which is to be selectively hydrogenated, is produced as the product of a conversion reaction in a reactor. A reactor refers to equipment used for chemical conversion. As such, several items identified as reactors may be combined to become a single entity that is also identified as a reactor, in that individual and combined entities may be characterized as equipment used for chemical conversion. Different types of reactors may be utilized to perform various reactions, which include a thermal pyrolysis reaction, partial oxidation reaction, indirect combustion reaction, and/or arc reaction.

The partial combustion reaction burns part of the feed to supply the heat to pyrolyse the remaining portion of the feed. The partial combustion reaction includes pyrolysis chemistry (e.g., thermochemical decomposition of feed at elevated temperatures in the absence of oxygen) and combustion chemistry (i.e., exothermic chemical reactions between a fuel and an oxidant), with both chemistries occurring at the same time and with the products of both chemistries being an integral part of the reactor product. An example of this process is German Patent No. 875198 and U.S. Pat. Nos. 3,242,223 and 7,208,647.

The indirect combustion reaction contacts a combustion product with the feed to be cracked in the reactor. As such, this process involves pyrolysis and combustion chemistry, but typically the combustion chemistry may occur at a different time or location and the pyrolysis chemistry, while occurring in the presence of combustion products, proceeds in a largely non-oxidative environment, resulting in the products of the two chemistries being an integral part of the reactor product. Examples of these types of reactors include G.B. Patent No. 834419, German Patent No. 1270537, and U.S. Pat. Nos. 3,419,632 and 7,208,647.

The arc reaction, which includes plasma arc reactors and electric arc reactors, typically involves only pyrolysis chemistry. Examples of these reactors are described in U.S. Pat. Nos. 1,860,624 and 7,119,240.

In general, a pyrolysis reaction is a thermal decomposition process in which pyrolysis feed is heated, generally in the absence of oxygen, to decompose the hydrocarbons into lower molecular weight hydrocarbon molecules. Pyrolysis typically occurs under pressure and at operating temperatures above 430° C. The term "pyrolysis" has also been applied to the decomposition of hydrocarbon material in the presence of superheated water or steam (hydrous pyrolysis), for example, in the steam cracking of hydrocarbon. That is, the thermal pyrolysis reaction involves heating a solid material (e.g., by combustion) and using the heated solid material to provide heat to crack the feed (e.g., via pyrolysis chemistry alone). In the thermal pyrolysis processes, the combustion products are typically maintained separate from the pyrolysis hydrocarbon products or effluent. This reaction involves various different types of reactors, such as U.S. Pat. Nos. 2,319,679; 2,678, 339; 2,692,819; 3,024,094; 3,093,697; 7,138,047 and 7,119, 240.

The pyrolysis or pyrolysis chemistry involves the conversion of hydrocarbons to unsaturates, such as ethylene and acetylene, which is an endothermic reaction requiring addition of heat. The terms "crack" and "cracking" may be used interchangeably with the terms pyrolyse and pyrolysis. In a pyrolysis reaction, $\geq 50\%$, $\geq 80\%$, or $\geq 90\%$, of this heat is provided by heat transfer via solid surfaces, such as tubulars or bed materials. Any combustion chemistry that occurs within the pyrolysis stream of a pyrolysis reactor provides a minority of the endothermic heat of pyrolysis, such as $<50\%$, $<20\%$, or $<10\%$ of the endothermic heat of pyrolysis.

The term "pyrolysis feed" means the composition, which may be a mixture, subjected to pyrolysis (e.g., hydrocarbon containing feed subjected to pyrolysis). In one embodiment, the pyrolysis feed is derived from a hydrocarbon feed (e.g., by separation of a portion from the hydrocarbon feed and/or optional diluents). The diluent may be a composition that is used to control partial pressure in the vapor phase. In certain embodiments, the diluent includes compounds that do not include any significant level of oxygen, because the presence of oxygen tends to produce undesirable levels of carbon oxides in the reactor product at the desired pyrolysis temperatures of the process. A preferred diluent is molecular hydrogen ($H_2$), particularly because hydrogen can also react with undesirable carbon by-products to reduce the formation of coke and tar-like by-products.

Some preferred feeds include one or more of methane, natural gas, aromatic feeds, and/or other suitable hydrocarbons containing feeds, as noted above.

As used herein, the terms "coke" and "soot" may refer to hydrocarbonaceous material that accumulates within the reactor during pyrolysis or to solid-phase hydrocarbonaceous materials that emerge from the reactor with the effluent. The hydrocarbonaceous material that accumulates within the reactor during pyrolysis may also be defined as the fraction of the pyrolysis feed that remains in a reactor and thus does not emerge from the reactor as effluent. The reactor product that does emerge may be referred to as the reactor effluent, which is at least a portion of the reactor product.

As a specific embodiment, a regenerative reactor may be utilized in the system of the present techniques upstream of the slurry conversion unit. Examples of reactors, which utilize at least pyrolysis chemistry, may include, but are not limited to, regenerative reverse-flow reactors as described in U.S. Patent App. Pub. No. 2007/0191664; and pyrolysis reactors as described in U.S. Pat. No. 7,491,250, U.S. Patent App. Pub. Nos. 2007/0144940 and 2008/0142409. If the process is a regenerative reverse-flow reactor, it may involve multiple steps repeated in sequence to form a cycle for the process. That is, the process may include two or more sequential steps, which include a heating step to heat the reaction zone and a pyrolysis step that converts the hydrocarbons into the reactor product (e.g., reactor effluent). The steps may involve passing streams over a solid material in fixed orientation (e.g., one or more reactor beds), which utilizes valves to alternate introduction of hydrocarbon and/or combustion streams into the internal portion of the reactor. The solid material may be designed to facilitate the process of heat addition and removal. Checker bricks, tiles and monoliths may be used as the solid materials within the reactor. Such materials form a network of passages that are used by the stream (e.g., gases) in each step to transit the region containing solid material. The heat addition step leaves a profile of temperatures in the solid material, that is, a temperature that varies along the path by which the gases transit the solid material. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. On average, the solid material is hottest at the end of the heating step. The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors do not operate in the steady state. That is, at any given location, the temperature changes. However, these reactors may be in a periodic steady state, meaning that the same cycling of temperatures occurs over and over as the reactor sequentially repeats the heating and pyrolysis steps.

The heat generated from the heating step may preferably be stored in a reactor bed or other solid material. The heat storing and transferring material may be a ceramic, which may include yttria, zirconia, alumina, and/or other refractory material capable of withstanding temperatures within the pyrolysis reactor. In the present techniques, the regenerative reverse-flow reactor may operate at peak pyrolysis gas temperatures of at least 1200° C., at least 1700° C., at least 2000° C., preferably at least 1400° C., at least 1500° C., or more preferably at least 1540° C. That is, the peak pyrolysis gas temperature ranges may include temperatures from 1200° C. to 2200° C., from 1450° C. to 1700° C., from 1500° C. to 1675° C., or from 1540° C. to 1650° C. In some reactions, it may even be still more preferable to expose the pyrolysis stream to heat using very short residence times, such as ≤0.1 second, to a temperature in excess of 1600° C. When the pyrolysis feed comprises methane, pyrolysis reactions typically include peak pyrolysis gas temperatures in excess of 1400° C. for the methane to react or convert. An exemplary preferred process may pyrolyze the feed stream within the reactor, such as at peak pyrolysis gas temperatures of from 1540° C. to 2200° C., and more preferably from 1600° C. to 1800° C. The process may involve operating the reactor at operating conditions having pressures ≥4 pounds per square inch gauge (psig) (27 kilo Pascal (kPa)), ≥15 psig (103 kPa), ≥36 psig (248 kilo Pascal (kPa)), ≥44 psig (303 kPa) or ≥103 psig (710 kPa), but may be ≤300 psig (2068 kPa), ≤163 psig (1124 kPa), or ≤150 psig (1034 kPa). Exemplary residence times preferably may be short, such as ≤0.5 second, ≤0.3 second and preferably ≤about 50 milliseconds or in the range of 0.5 seconds to 0.001 seconds.

In an embodiment, the reactor may include components comprised of yttria. In an embodiment, one or more of the reactor beds include separate conduits for separately channeling flow of feed components or regeneration fluid components (e.g., combustion stream components) through the reactor beds. Preferably, each reactor bed includes separate conduits. The separate flow channels in the reactor beds can further comprise flow barriers that effectively function as conduit walls to prevent cross flow or mixing of fluids between channels. Each reactor bed preferably includes multiple channels, which may preferably be in parallel flow arrangement.

As noted above, the present techniques differ in at least one particular way from many conventional conversion processes to the extent that this pyrolysis process may include one or more steps in a cycle during hydrocarbon processing mode. One step can be referred to as a heating step (e.g., involving heating and regenerating). The heating step involves reacting combustion streams, which may include two or more individual feeds that are to be combined to form a combustion reaction or a mixture of the two or more feeds, such as a fuel that does not contain oxidants (e.g., $O_2$) or non-combustible non-volatiles and a combustion oxidant that may include an oxygen or oxygen containing fluid. The fuel stream may be a hydrogen-containing composition of hydrogen, hydrocarbon, or a mixture thereof. The hydrocarbon can be the same or different from the hydrocarbon used in the pyrolysis feed. Another step can be referred to as the pyrolysis step (e.g., pyrolysis or hydrocarbon conversion mode). These different steps may be performed in sequence to form a cycle, which is then repeated as part of the normal hydrocarbon processing operations. The cycle may be performed continuously, semi-continuously, periodically or even as a batch operation. Accordingly, a cycle includes the time spent in heating step plus time spent in pyrolysis step plus any time needed to switch between steps or for additional steps before the repeat of the sequence. Typical cycle times may be in the range of 1 to 240 seconds, or in the range of 2 to 60 seconds. The heating and pyrolysis steps may have equal durations or may be adjusted to have different durations.

In accord with the present techniques, the regenerative pyrolysis process tends to produce product gas mixtures with higher concentrations of alkynes, particularly acetylene as compared to more conventional thermal cracking processes such as steam cracking. This first converter feed (e.g., alkyne rich gas mixture) is more efficiently upgraded to ethylene using the slurry conversion unit and process. As noted earlier the hydrogenation process can be carried out directly using the vapor phase pyrolysis product or the liquid phase pyrolysis product as the first converter feed. Similarly, the first converter feed may be a vapor phase pyrolysis product dissolved into a liquid carrier fluid and/or solvent using a suitable gas liquid contacting device. In either embodiment, the slurry conversion system configuration is particularly well suited to capture the heat generated during hydrogenation for steam generation.

After the pyrolysis conversion stage, at least a portion of the reactor product, e.g., a portion (e.g., reactor effluent) which comprises $C_2$ unsaturates, hydrogen and may optionally include carbon dioxide and/or carbon monoxide, is conducted away from a conversion reactor to an optional upgrading stage. The upgrading stage may include a first separated portion that comprises, e.g., one or more of hydrocarbons (such as saturated hydrocarbon and/or those containing one or more heteroatoms), diluent, non-volatiles, saturated hydrocarbons, and hydrogen, etc. Optionally, a second portion is separated from the second converter feed, the second portion comprising, e.g., a portion of the second converter feed that is not in the vapor phase at the downstream end of the reactor. Optionally, the second portion remains in the conversion stage (e.g., in the reactor), e.g., as coke. In this embodiment, the first converter feed, thus derived from the reactor effluent by the separations occurring in the upgrading stage is conducted away to the slurry conversion unit. In embodiments where, e.g., (i) no portion of the reactor product remains in the reactor and/or (ii) optional upgrading is not performed, the first converter feed comprises, consists essentially of, or even consists of the reactor products. In another embodiment, the first converter feed comprises, consists essentially of, or even consists of that portion of the reactor products which are in the vapor phase at the downstream end of the conversion reactor.

In one embodiment, upgrading includes means for removing from the reactor effluent one or more of hydrocarbon (such as, saturated hydrocarbon and/or those containing one or more heteroatoms), diluent, non-volatiles, and hydrogen, etc. For example, the upgrading can include one or more of a tar and/or solid removal means, compression means, adsorption means, distillation means, washing means, or drying means. While upgrading can encompass conventional processing, e.g., conventional separation means, the present techniques are not limited thereto. Separation means can be used, e.g., for removing condensable species (e.g., condensable hydrocarbon) from the reactor effluent. Such condensable species may include vaporized liquids that condense, such as benzene, or those that can be separated via, e.g., cooled separations for example, adsorption, vapor liquid separators, flash drums etc. Suitable separations means include conventional distillation or refrigerated distillation means, such as one or more of demethanators and $C_2$ splitters, etc., but the present techniques are not limited thereto. The present techniques is compatible with low-pressure demethanizers and high-pressure demethanizers (e.g., those operating at a pressure≥3.5 MPa), along with contacting the reactor effluent or a portion thereof with a fluid having a pH>7.0.

In an embodiment, at least a portion of any light-gas in the reactor effluent (e.g., one or more of molecular hydrogen, light saturated hydrocarbon such as methane, carbon dioxide, hydrogen sulfide, etc.) can be removed in upgrading stage. Suitable light-gas removal means include one or more of separation, basic wash (e.g., caustic wash or amine scrubbing), or drying etc. Optionally, the separation means includes one or more of pressure swing absorption, membranes and/or cryogenic distillation, electrochemical separation, or liquid absorption. Light-gas separation means may be used to separate hydrogen, carbon monoxide, methane, nitrogen, carbon dioxide or other light gases. Optionally, the removed light gas can be used, e.g., to adjust the stoichiometry of the first converter feed (e.g., by increasing the hydrogen and/or diluent content, etc.), as a stripping medium (e.g., for upgrading one or more sources from which the first converter feed is derived, such as by stripping upstream of the reactor), etc. For example, should the reactor effluent contain more hydrogen than is needed for processing the products, at least a portion of the hydrogen in the reactor effluent can be removed, e.g., by partially cooling the reactor effluent (optionally at essentially constant pressure) to condense at least a portion of the reactor effluent and then separating therefrom a vapor comprising hydrogen. The separated hydrogen can be conducted away and utilized, e.g., for producing the first converter feed, or for converting at least a portion of the reactor effluent acetylene to ethylene.

Optionally, upgrading includes means for removing at least a portion of any water present in the reactor effluent, e.g., by one or more of a methanol treatment, such as those described in Belgian Patent No. 722,895, adsorption, extraction by diethylene glycol, etc. For example, the upgrading stage can include one or more driers located, e.g., downstream of caustic treatment, for removing at least a portion of the water, including conventional driers, e.g., molecular sieve dryers.

When it is desirable for the first converter feed to have a higher pressure and/or lower temperature than the reactor effluent, upgrading stage can include, e.g., means for cooling and then compressing the portion of the reactor effluent conducted away from reactor to produce the first converter feed. For example, in embodiments where the conversion reactor has an outlet pressure<the inlet pressure of downstream stages, the upgrading stage can include, e.g., compressing at least the portion of the reactor effluent from which the first converter feed is derived to achieve the desired inlet pressure. Should the reactor effluent comprise acid gases (e.g., $CO_2$ and/or $H_2S$), these can be removed, e.g., downstream of the compression—a desirable location because the gas volume has been reduced significantly during compression. Conventional methods are suitable for removing acid gases, e.g., caustic treatment, but the present techniques are not limited thereto. Acid gases separated from the reactor effluent can be conducted away, e.g., for storage or further processing such as in a Claus plant.

The upgrading stage can also be utilized to produce the first converter feed by combining at least a portion of the reactor effluent with added species, such as molecules obtained from other stages of the process. For example, at least a portion of the product of the downstream conversions of products can be separated and conducted upstream to the upgrading stage to adjust the composition of the in the first converter feed. In one embodiment, the first converter feed comprises a portion of the reactor effluent to be conducted to the further processing stages and further comprises one or more of methane, ethane, carbon monoxide, carbon dioxide or hydrogen recycled, e.g., from downstream of the products stages. The upgrading stage can include means for separating carbon monoxide, carbon dioxide or hydrogen from the reactor effluent, all or a portion of which can be utilized to increase the first converter feed's content. This may occur when low-temperature separations are utilized to remove undesired low-boiling point species from the reactor effluent.

In an embodiment, at least a portion of the molecular hydrogen, saturated hydrocarbon, diluent, etc., separated from $C_2$ unsaturates in upgrading stage may be recycled, e.g., by combining such separated species with one or more of the first converter feed or feed to the conversion reactor. Exemplary embodiments of a slurry conversion system are described further below in FIGS. 2-4.

Figure 2:
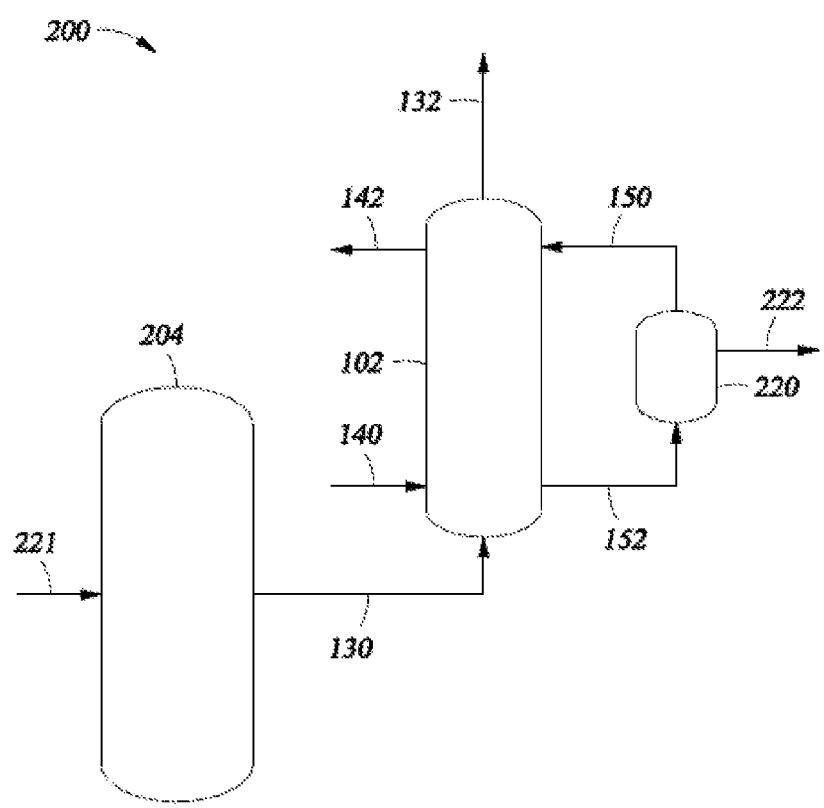
FIG. 2 is a simplified diagrammatic illustration of an exemplary process for converting a feed into conversion products in accordance with an embodiment of the present techniques.

FIG. 2 is a simplified diagrammatic illustration 200 of an exemplary process for converting pyrolysis feed containing hydrocarbons into a product, such as ethylene in accordance with an embodiment of the present techniques. In this illustration 200, a particular configuration of unit operations (i.e. units) are coupled together to convert a feed into the product. These units may include a conversion reactor 204, a slurry conversion unit 102, and carrier fluid regeneration unit 220. It should be noted that the process may optionally include a solid removal unit, a compressor, a product separation unit disposed between the conversion reactor 204 and the slurry conversion unit 102. The process will now be explained in more detail.

A pyrolysis feed is provided via line 221 to the conversion reactor 204, which may be one or more of a regenerative reverse flow reactor, partial oxidation reactor, indirect combustion reactor, arc reactor or other suitable reactor. The pyrolysis feed may optionally be adjusted to have hydrogen content within a predetermined range. The pyrolysis feed may include hydrogen gas ($H_2$) in an amount that provides a preferred ratio of hydrogen gas ($H_2$) moles to the total moles of carbon (C) in the hydrocarbon components of the pyrolysis feed. The ratio of hydrogen to carbon ($H_2$/C) may be from 0.0 or 0.1 to 5.0, such as 0.0, 0.1, 1.0, 2.0, 3.0, 4.0, 5.0, or values in between. Combining the hydrogen content of the hydrogen gas to the hydrogen and carbon contents of the hydrocarbon components of the pyrolysis feed may result in a total atomic ratio of hydrogen (H) to carbon (C) in the pyrolysis feed that is in the range of 0.1 to 20 or in the range of 3 to 15. For example, the weight percent of total hydrogen in the pyrolysis feed may be from 8 wt % to 54 wt %. Accordingly, the conversion reactor 204 may have different piping configurations to provide combustion feed (e.g., fuel) and the pyrolysis feed separately, depending on the specific configuration.

The reactor effluent or portion of the reactor product from the conversion reactor 204 may be subjected to various upgrading processes to form the first converter feed. In this embodiment, the first converter feed may be conducted away via line 130. In other embodiments, impurities may be withdrawn as products or bottom streams from the reactor effluent to form the first converter feed via other vessels (not shown). These vessels may be coupled in fluid communication between the conversion reactor and the slurry conversion unit.

The slurry conversion unit 102, as noted above, may optionally receive the first converter feed from the product separation unit (not shown). The slurry conversion unit 102 selectively hydrogenates the acetylene to ethylene without significantly hydrogenating the ethylene to ethane. In one embodiment, a conversion product of ≥50 wt % of ethylene may be conducted away from the slurry conversion unit 102 for storage or further processing. In addition, a purification unit and ethylene polymerization unit (not shown) may be coupled to the slurry conversion unit 102. As an example, the purification unit may include a demethanator tower (to remove $H_2$, $CH_4$, $N_2$ and CO) and a $C_2$ splitter to remove ethane and upgrade ethylene to polymer grade ethylene. The purification unit may also include $C_2$ or $C_3$ refrigeration train, compression and additional distillation towers. The ethylene polymerization unit may be a catalytic reactor, which may include a fluidized particulate catalyst for gas phase processing and/or molecular catalysts dispersed into a liquid solvent for solution processing. The process may involve a catalyst, solvent and the feed stream, as discussed above. Further, a portion of the acetylene in the reactor effluent may optionally be combined with other process steps to form other products, such as vinyl esters, ethylene, benzene, acetaldehyde, propanal, propanol, acrylic acid, and/or the like.

The reactions to convert the acetylene to ethylene may produce green oil and other contaminates. Accordingly, the slurry conversion unit 102 may include an optional carrier fluid regeneration unit 220 to remove at least a portion of the impurities from the liquid phase of the slurry (e.g., byproducts of the first converter feed and second converter feed). The carrier fluid regeneration unit 220 may be in fluid communication with the slurry conversion unit 102 via lines 150 and 152. The carrier fluid regeneration unit 220 may involve decontaminating the carrier fluid and recycling the decontaminated carrier fluid to the slurry conversion unit 102. For instance, the carrier fluid regeneration unit 220 may involve heating the carrier fluid (e.g., solvent) to vaporize the carrier fluid from the slurry, removing the vaporized carrier fluid, recycling the carrier fluid to the slurry conversion unit 102, and removing contaminates as a bottoms stream. Also, the carrier fluid regeneration unit 220 may include cooling the slurry to condense contaminates, recycling the decontaminated carrier fluid to the slurry conversion unit 102, and removing contaminates as a bottom stream. These contaminates may be removed via line 222, while the decontaminated carrier fluid may be recycled to the slurry conversion unit 102 via line 150.

As part of this system, energy may be recovered from the heat generated by the reactions to heat a utility fluid passing through the slurry conversion unit 102 via lines 140 and 142. These lines 140 and 142 may be in fluid communication with other heat exchangers (not shown) as part of the system. The heat exchangers can be integral to the flow of feed to the conversion reactor or other equipment downstream of the conversion reactor. As an example, the feed to the conversion reactor may be preheated by the heat exchanger upstream of flowing to the slurry conversion unit or downstream of the slurry conversion unit. In addition, the lines 142 may be integrated with a steam cracking reactor (e.g., to preheat feed, as a diluent, and/or as part of the heat recovery system) or other equipment associated with the system. By recovering the heat from the reactions in the slurry conversion unit, the heat may be utilized by a conversion reactor to reduce the feed utilized for heating, which may result in the fuel being utilized in the conversion reactor as feed. That is, enhancing the efficiency of the system.

Further, in some embodiments, the slurry conversion unit 102 may be integrated with additional acetylene conversion unit, such as another slurry conversion unit or a finishing acetylene conversion unit (e.g., a fixed bed acetylene conversion unit and/or microchannel acetylene conversion unit). The finishing acetylene conversion unit may be in fluid communication with one or more units, such as a compressor, stream recycle components, desorption unit and/or separation unit.

Figure 3:
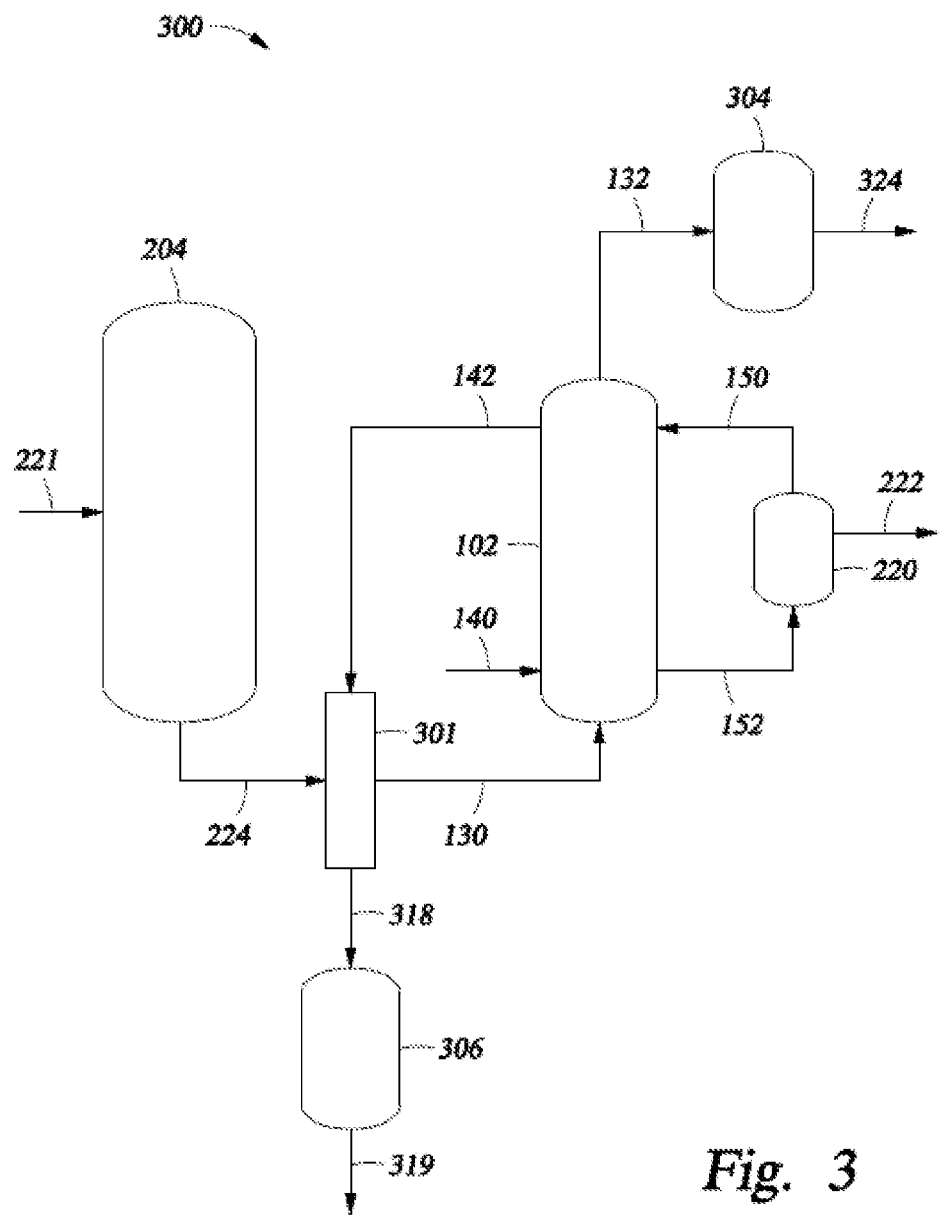
FIG. 3 is a simplified diagrammatic illustration of another exemplary process for converting a feed into conversion products in accordance with an embodiment of the present techniques.

FIG. 3 is a simplified diagrammatic illustration of an exemplary recovery configuration 300 that may be utilized with the present techniques. In this configuration 300, a particular configuration of units are coupled together to convert the first converter feed (e.g., a portion of the reactor effluent) and recover steam in an enhanced manner. The configuration 300 includes the units, such as the conversion reactor 204, a slurry conversion unit 102, and carrier fluid regeneration unit 220, which operate as noted above. However, in this configuration 300, a heat exchanger 301 and a steam drum 306 are integrated into the system to recover energy from the process. Also, the configuration includes a finishing acetylene conversion unit 304 coupled in series together with the slurry conversion unit 102 to further enhance the conversion process. The process will now be explained in more detail.

In this configuration, reactor effluent is passes via line 224 to a first heat exchanger 310. The heat exchanger may be a shell-in-tube heat exchanger or any other suitable indirect heat exchange unit. The cooled reactor effluent, which is the first converter feed for this embodiment, is passed via line 130 to the slurry conversion unit 102. The vapor product from this unit 102 is provided via line 132 to a finishing acetylene conversion unit 304. The finishing acetylene conversion unit 304 may be a second slurry conversion unit, a microchannel acetylene conversion unit, a fixed bed acetylene conversion unit or combination thereof. The use of a finishing acetylene conversion unit may reflect an economic optimization decision for a given system configuration. For example, if the volume of acetylene in the first converter feed is too large for cost effective conversion in a single conversion unit, multiple stages of acetylene conversion units can be utilized. Regardless, the product from the finishing acetylene conversion unit may be provided via line 324 for further processing, as noted above.

To recover energy from this process, the slurry conversion unit 102 may be coupled to one or more heat recovery stages to generate steam. As an example, the configuration 300 has the slurry conversion unit 102 in fluid communication with the heat exchanger 301 and steam drum 306 to generate steam from the reactions in this process. The utility fluid is provided to the slurry conversion unit 102 via line 140, heated within the slurry conversion unit 102, as noted above. Then, the heat utility fluid is passed to the heat exchanger 301 via line 142, which further heats the heated utility fluid via indirect heat transfer from the reactor effluent passing from lines 224 to line 130. The heated utility fluid is then passed to a steam drum 306, and steam is removed via line 319 for further use. This use may include generating electricity via turbines, which may be utilized to power compressors (e.g., compressor 208) and the like.

In this configuration 300, the slurry conversion unit 102 may operate at first converter feed levels ranging from 0.5 to 30 mol % acetylene, or ranging from 0.5 to 15 mol % acetylene. The slurry conversion unit 102 may operate at pressures from 15 psig (103.4 kPa) to 1000 psig (6900 kPa), at inlet temperatures of 50° C. to 400° C. and may utilize catalyst comprising group VI or VIII catalysts. Conversion levels for the slurry conversion unit 102 may range from 70 wt % to 100 wt % acetylene conversion and may have selectivity to ethylene from 70 wt % to as high as 98 wt % to ethylene. The finishing acetylene conversion unit 304 may convert remaining levels of acetylene at essentially 100 wt % conversion of the acetylene. This finishing acetylene conversion unit 304 may be in fluid communication with the one or more units, such as the acetylene conversion unit or other units downstream of the acetylene conversion unit. The acetylene conversion unit may include a hydrogenation unit.

Figure 4:
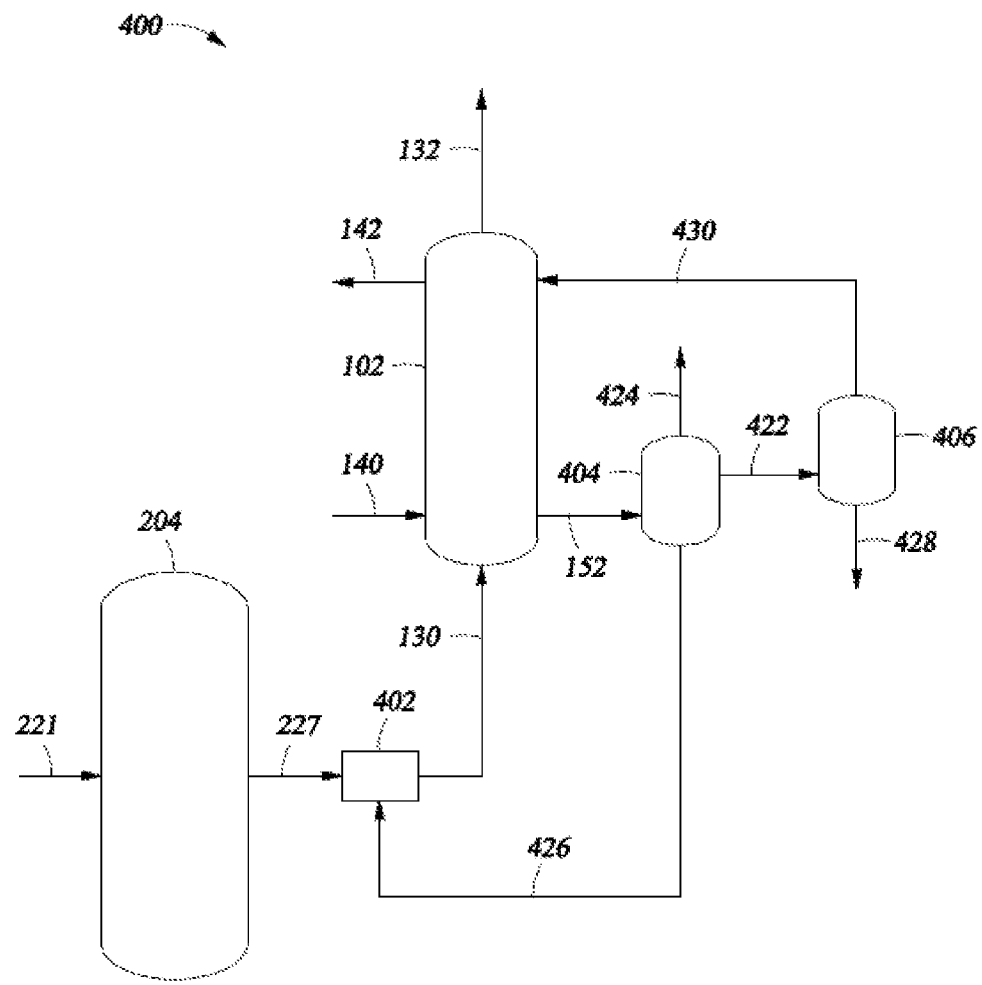
FIG. 4 is yet another simplified diagrammatic illustration of an exemplary process for converting a feed into conversion products in accordance with an embodiment of the present techniques.

FIG. 4 is a simplified diagrammatic illustration of yet another exemplary recovery configuration 400 that may be utilized with the present techniques. In this configuration 400, a particular configuration of units are coupled together to convert the first converter feed (e.g., derived from the reactor effluent) and recover steam in an enhanced manner. The configuration 400 includes the units, such as the conversion reactor 204 and a slurry conversion unit 102, which operate as noted above. However, in this configuration 400, an absorbent is mixed with a portion of the reactor effluent in an absorption unit 402 to form the first converter feed prior to the slurry conversion unit 102. In addition, various regeneration units, such as a carrier fluid regeneration unit 404 and a catalytic particle regeneration unit 406, are utilized to separate the carrier fluid and/or catalytic particles from the portion of the slurry that is passed to the regeneration units. The process will now be explained in more detail.

In this configuration, reactor effluent is provided from the conversion reactor 204, passed to the absorption unit 402 via line 227 and combined with the carrier fluid to form the feed. The absorption unit 402 may be a manifold, sparger, static mixer, or other suitable gas liquid contactor unit that combines the absorbent with the reactor effluent.

The first converter feed is provided to the slurry conversion unit 102 via line 130. The vapor product from this unit 102 is provided via line 132 for further processing, which may include a finishing acetylene conversion unit or other processing steps, as noted above. However, a portion of the slurry in the second interior region may be provided via line 152 to the carrier fluid regeneration unit 404. The carrier fluid regeneration unit 404 may separate the carrier fluid from the slurry in manner similar to the discussion above. The separation may include a pressure letdown device, stripping equipment, and or suitable fractionation towers to efficiently disengage products and unreacted feed from the carrier fluid. For example, the separation unit may include a stripping tower, distillation column and/or flash drum. The carrier fluid may be passed via line 426 to the absorption unit 402, while the remaining slurry may be passed to the catalytic particle regeneration unit 406.

The catalytic particle regeneration unit 406 may separate the catalytic particles from any other contaminates remaining from the slurry and then further treat the catalysts to restore a high level of activity. Other additional steps include drying the catalyst particles of residual carrier fluid (e.g., solvent) by heating or stripping with a hot gas, removal of strongly bound carbonaceous deposits by oxidation or combustion, and/or redispersion of the active metals by treatment with catalyst redispersion agents such as chlorine or chlorine containing compounds. The regeneration procedure typically involves multiple steps and vessels. Catalyst can be conveyed between the vessels pneumatically or by other means. The catalytic particles may be passed via line 430 to the slurry conversion unit 102, while contaminates may be passed to the other units for further processing via line 428.

Figure 5:
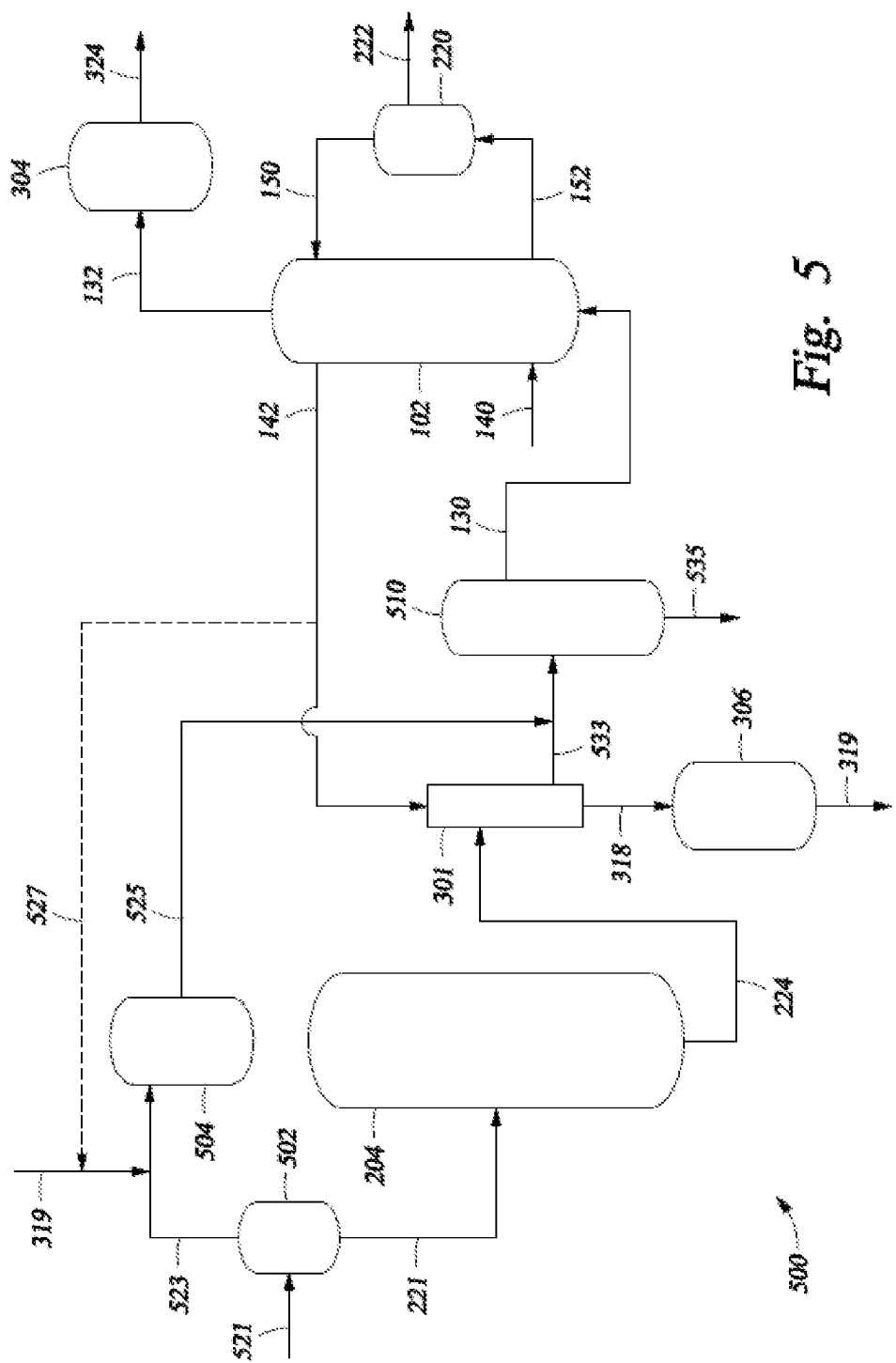
FIG. 5 is a simplified diagrammatic illustration of an exemplary process for integrating heat recovery in a system for converting a feed into conversion products in accordance with an embodiment of the present techniques.

FIG. 5 is a simplified diagrammatic illustration 500 of an exemplary process for that integrates the heat recovery into other units within the system. In this illustration 500, a particular configuration of units are coupled together to convert a hydrocarbon feed to conversion products. These units may include a separation unit 502, a first conversion reactor 204, a second conversion reactor 504, a separation unit 510 and other units 102, 220, 301, 304 and 306, which operate as noted above. The second conversion reactor 504 may be a steam cracking furnace or other reactor that produces products having different distributions of compounds as compared to those produced from the first conversion reactor 501. By integrating these different reactors together, the system may provide additional flexibility management and processing of a given feed, as each reactor may be configured differently. The process will now be explained in more detail.

A hydrocarbon feed is provided via line 521 to the feed separation unit 502. The hydrocarbon feed may be crude oil, a fraction of crude oil components, distillates or other suitable hydrocarbons. The feed separation unit 502 may divide the hydrocarbon feed into a first portion or mixture (e.g., the first pyrolysis feed) provided via line 221 to the first conversion reactor 204 and a second portion or mixture (e.g., a second pyrolysis feed) provided via line 523 to the second conversion reactor 504. The feed separation unit 502 may be a flash drum separator, an atmospheric distillation column, and/or a fractionator. After conversion, the second reactor effluent (e.g., at least a portion of the second reactor product from the second conversion reactor 504) may be passed via line 525 to be combined with the first reactor effluent (e.g., at least a portion of the first reactor product from the first conversion reactor 204) from the heat exchanger 301 via line 533. The reactor effluent (e.g., first reactor effluent and second reactor effluent) passes to a separation unit 510, which may remove various contaminates via line 535, such as tar and/or solids, to produce the first converter feed. Then, the first converter feed is processed in the slurry converter unit 102 and other various units 220 and 304, as noted above.

As a further enhancement involving heat recovery, the heated utility fluid from slurry conversion unit 102 is provided via line 142 for use in other units, such as the second conversion reactor 504. As an example, the heated utility fluid may be provided via line 142 to the heat exchanger 301 and the steam drum 306. The heated utility fluid may then be added to the second pyrolysis feed via lines 319 and 523. In this manner, the energy that is typically not recovered in other processes may be utilized with this integrated system to enhance operations. In yet another embodiment, the heated utility fluid from slurry conversion unit 102 is provided via line 142 directly to the second conversion reactor 504. The heated utility fluid may then be added to the second pyrolysis feed via lines 319, 523 and 527.

This integration of the different reactors with the slurry conversion unit may enhance the operation of the system. For instance, the heat recovered from the slurry conversion unit may be utilized to heat the feeds to one or both of the reactors. Further, the heated utility fluid may be utilized in one or more of the reactors as a diluent. Regardless, the recovered heat may be utilized to lessen the amount of fuel required by the system to convert the feed (e.g., by one or both of the reactors).

In addition, certain types of reactors may be integrated to provide additional benefits. For instance, if the second conversion reactor 504 is a steam cracking reactor and the first conversion reactor 204 is a high temperature thermal pyrolysis reactor, then integration of the reactors provides further efficiencies. In particular, the products from the second conversion reactor 504 may predominately include ethylene with lower concentrations of acetylene. The products from the first conversion reactor 204 may predominately include acetylene with lower concentrations of ethylene. By combining these products together, the acetylene concentration for the combined stream may be lowered. As a result, the acetylene concentration may be more easily managed below the detonation limits, which provides further flexibility in the operation of the system. Further, the preheating of the utility fluid may lessen the fuel need for the system, as noted above.

To further enhance the process, the present techniques may include a method to manage the ethylene to acetylene mole ratio for the reactor effluent upstream of the slurry conversion unit. For instance, in one or more embodiment, the conversion reactor may expose a hydrocarbon feed to a peak pyrolysis gas temperature≥1500.0° C. to produce a reactor product. The reactor product or reactor effluent may include ≥2 mol % acetylene, ≥4 mol % acetylene, ≥20 mol % and/or ≥30 mol % acetylene. To manage the ethylene to acetylene mole ratio, the ethylene to acetylene mole ratio of the reactor effluent may be adjusted to have an ethylene to acetylene mole ratio≤2:1, ≤5:1, ≤10:1, or ≤15:1 of the acetylene and ethylene in the reactor effluent, which may be managed via recycle, adjusting the pressure for the conversion and the like, wherein the feed to the slurry conversion unit has ≥2 mol % of acetylene. The ethylene to acetylene mole ratio may have a lower limit of ≥30:1, ≥25:1, or ≥20:1 of the acetylene and ethylene in the reactor effluent. Then, the adjusted reactor effluent may be passed to the slurry conversion unit to produce ethylene from hydrogenation of the adjusted reactor effluent. This adjustment to the ethylene to acetylene mole ratio may be managed by recycling ethylene to the process. That is, in one embodiment, the ethylene produced by the system may be combined with the reactor effluent to adjust this ratio.

Alternatively or in addition to such a recycle, one or more conversion reactors that operate at different temperatures to produce different products may be utilized to provide this functionality. These conversion reactors along with a slurry conversion unit may be operated as a system that enhances operations because of the recovery of heat along with the management of the products with a lessening of the recycled product (e.g., ethylene). As an example, a first conversion reactor may expose a first hydrocarbon feed to a peak pyrolysis gas temperature≥1500.0° C. to produce a first reactor product. This first reactor effluent (e.g., portion of the first reactor product) may include ≥2 mol % acetylene, ≥4 mol % acetylene, ≥20 mol % acetylene, or ≥30 mol % acetylene, but below the auto-detonation limits for given operating conditions. A second conversion reactor may expose a second hydrocarbon feed to a peak pyrolysis gas temperature≥700.0° C. to produce a second reactor product. The second reactor effluent (e.g., portion of the second reactor product) may include ≤2 mol % acetylene, ≤1 mol % acetylene or even ≤0.5 mol % acetylene. These reactor effluents may be combined to produce a combined reactor effluent. The combined reactor effluent may also include a recycled stream of additional diluent, such as ethylene from the slurry conversion unit to further manage the reactor effluents. The acetylene, hydrogen, carrier fluid and catalytic particles may be combined to produce slurry in a slurry conversion unit, wherein the acetylene is derived from the combined reactor product. The slurry conversion unit may expose the slurry to an average hydrogenation reaction temperature greater than or equal to 125° C. to produce a vapor product comprising ethylene.

To monitor this process, various measurement devices may be utilized, which may include various sensors or one or more gas chromatography (GC) devices. These devices may be coupled to various lines within the system to provide the concentrations for the various effluents through the process. For instance, a first GC device may determine a first ethylene to acetylene mole ratio for the first reactor effluent, while a second GC device may determine a second ethylene to acetylene mole ratio for the second reactor effluent. Another GC may be utilized to monitor the concentration of the combined effluents. Then adjustments may be made based upon one or more of these concentrations. For instance, the adjustments to the amount of recycle within the process may be based on the determined first ethylene to acetylene ratio and the determined second ethylene to acetylene ratio. These mole ratios may be compared to adjust the recycled amount of a diluent or other product to the process.

As additional embodiments, the heat recovered from this system may be utilized to enhance the operation of the system. For instance, the recovered heat from the slurry converter unit may be utilized to reduce the amount of reactants (e.g., fuel and/or oxidants) or hydrocarbon feed provided to one or more of the reactors. Further, the recovered heat in the form of a heated utility fluid may be utilized as a diluent by combining the heated utility fluid with the second mixture upstream of the second conversion reactor. This may provide heat to the feed to this reactor along with other benefits derived from diluents (e.g., as noted in steam cracking processes). In addition, the recovered heat in the form of a heated utility fluid may be utilized to heat one or more of the feeds via indirect or direct heat exchange upstream of the respective reactor.

The invention is further defined in terms of the following embodiments.

1. An acetylene conversion method comprising:
combining acetylene, molecular hydrogen, carrier fluid and catalytic particles to produce slurry in a slurry conversion unit; and exposing the slurry to operating conditions that include an average hydrogenation reaction temperature greater than or equal to 125° C. to produce a vapor product comprising ethylene; and extracting heat from the slurry conversion unit via indirect heat exchange with a utility fluid.

2. A method of processing hydrocarbons to produce ethylene comprising:

combining (i) a first converter feed containing acetylene and molecular hydrogen with (ii) a second converter feed comprising a carrier fluid and catalytic particles to produce slurry in a slurry conversion unit; and reacting the acetylene with the molecular hydrogen in the presence of the catalytic particles in the slurry at operating conditions that include an average hydrogenation reaction temperature greater than 125° C. to produce a vapor product comprising ethylene; and extracting heat from the slurry conversion unit via indirect heat exchange with a utility fluid.

3. The method of embodiment 2, wherein the first converter feed comprises at least 2 mol % acetylene based on the total first converter feed.

4. The method of any one of embodiments 1 to 3, wherein the catalytic particles convert at least a portion of the acetylene to ethylene at operating conditions sufficient to yield a conversion rate of at least 0.4 moles/hour/cc of catalytic particles.

5. The method of any one of embodiments 1 to 3, wherein the catalytic particles convert at least a portion of the acetylene to ethylene at operating conditions sufficient to yield a conversion rate of at least 2 moles/hour/cc of catalytic particles.

6. The method of any one of embodiments 1 to 5, further comprising utilizing at least a portion of the extracted heat to perform one or more of (i) generating steam from the heated utility fluid, (ii) combining the heated utility fluid with a pyrolysis feed provided to a conversion reactor upstream of the slurry conversion unit, and (iii) heating the pyrolysis feed via the heated utility fluid.

7. The method of any one of embodiments 1 to 5, further comprising utilizing at least a portion of the extracted heat to reduce one or more a pyrolysis feed and a combustion feed utilized in a conversion reactor upstream of the slurry conversion unit.

8. The method of any one of embodiments 1 to 7, further comprising passing the utility fluid through a bank of heat exchange tubes within the slurry conversion unit to extract the heat.

9. The method of any one of embodiments 1 to 8, wherein the utility fluid is one or more of water and steam.

10. The method of any one of embodiments 1 and 9, further comprising:

removing at least a portion of the slurry from the slurry conversion unit;

regenerating the separated slurry; and combining at least a portion of the regenerated slurry with the slurry in the slurry conversion unit.

11. The method of any one of embodiments 1 and 10, further comprising:

separating at least a portion of the carrier fluid from the slurry in the slurry conversion unit;

regenerating the separated carrier fluid; and utilizing at least a portion of the regenerated carrier fluid to produce the slurry.

12. The method of any one of embodiments 1 and 5, further comprising exposing a pyrolysis feed to temperatures greater than 1500° C. under pyrolysis conditions to produce at least a portion of the acetylene provided to the slurry conversion unit.

13. The method of any one of embodiments 1 to 12, wherein the slurry comprises between 2 wt % and 40 wt % catalyst particles based on the total weight of the slurry.

14. The method of any one of embodiments 1 to 13, wherein the carrier fluid comprises a solvent that solubilizes green oil.

15. The method of any one of embodiments 1 to 14, wherein the carrier fluid comprises a solvent that absorbs acetylene at a higher selectivity as compared to ethylene.

16. The method of any one of embodiments 1 to 15, wherein the carrier fluid has a dipole moment in the range from 2.0 D to 4.0 D.

17. The method of any one of embodiments 1 to 16, wherein the catalytic particles convert at least a portion of the acetylene to ethylene at operating conditions sufficient to yield a conversion rate of at least 5 moles/hour/cc of catalytic particles.

18. The method of any one of embodiments 1 to 17, wherein the catalytic particles are in the form of spherical or semi-spherical particles having an average diameter≤150 micrometers.

19. The method of any one of embodiments 1 to 18, wherein the average hydrogenation reaction temperature is in the range of 200° C. to 300° C.

20. The method of any one of embodiments 1 to 19, wherein the catalyst particles comprise a catalytic material that has an acetylene conversion in excess of 80% at operating conditions.

21. The method of any one of embodiments 1 to 20, wherein the catalyst particles comprises particles having an average diameter in the range of ≥10 μm and ≤150 μm.

22. The method of any one of embodiments 6 and 7, further comprising:

passing the combustion feed to the conversion reactor during a heating step; and reacting the combustion feed to form combustion products and combustion heat within the conversion reactor;

removing the combustion products from the conversion reactor;

passing the pyrolysis feed to the conversion reactor; and exposing the pyrolysis feed to the combustion heat within the conversion reactor to produce a reactor effluent comprising at least a portion of the acetylene.

23. The method of embodiment 22, further comprising separating the acetylene from the reactor effluent.

24. The method of any one of embodiments 1 to 23, comprising passing the vapor product to a finishing acetylene conversion unit to convert the remaining acetylene in the vapor product to ethylene.

25. The method of any one of embodiments 1 to 24, wherein each of the catalytic particles comprise at least 2 wt % of an active catalytic material comprised of one or more metals selected from Group 8 to 10 of the Periodic Table based on the total weight of the catalytic particle.

26. The method of any one of embodiments 1 to 25, wherein the catalytic particles comprise >0.5 wt % palladium or platinum based on the total weight of the catalyst particle.

27. The method of any one of embodiments 1 to 26, wherein each of the catalytic particles comprise at least 10 wt % of a metal selected from Groups 8 to 10 of the Periodic Table based on the total weight of the catalytic particle.

28. The method of any one of embodiments 1 to 27, wherein the catalyst particles have selectivity to olefin in excess of 50 mol % at operating conditions.

29. The method of any one of embodiments 1 to 28, wherein the method has selectivity to green oil of less than 10 wt % at operating conditions.

30. The method of any one of embodiments 2 and 3, wherein the first converter feed includes hydrogen at a $H_2/C_2H_2$ molar feed ratio of from 0.5 to 50.

31. The method of any one of embodiments 1 to 30, wherein the slurry conversion unit is operated in a churn turbulent regime.

32. The method of embodiment 31, wherein the churn turbulent regime has superficial gas velocities above about 10 cm/sec.

33. The method of any one of embodiments 1 to 32, wherein the operating conditions includes a pressure≥303 kPa and ≤2068 kPa.

34. A system for processing hydrocarbons to produce ethylene comprising:
a slurry conversion unit configured to convert a first converter feed into ethylene and having:
   a housing forming an interior region;
   an inlet medium configured to:
      divide the interior region within the housing into a first interior region and a second interior region;
      restrict flow of a second converter feed from the second interior region into the first interior region; and
      permit the flow of the first converter feed from the first interior region into the second interior region;
   an inlet means configured to pass a first converter feed from a location external to the housing to the first interior region;
   an outlet means configured to pass vapor products from the second interior region to a location external to the housing;
   a solvent removal means configured to remove at least a portion of the slurry from the second interior region to a location external to the housing;
   a solvent injection means configured to pass a solvent into the second interior region; and
a solvent regeneration unit in fluid communication with the second interior region of the slurry conversion unit and configured to:
   receive slurry from the second interior region from the solvent removal means;
   separate solvent from contaminates in the slurry; and
   pass the decontaminated solvent to the solvent injection means.

35. The system of embodiment 34, further comprising a conversion reactor in fluid communication with and upstream of the slurry conversion unit and configured to expose a pyrolysis feed to a peak pyrolysis gas temperature≥1500.0° C. within the conversion reactor to produce a reactor effluent.

36. The system of embodiment 35, further comprising a solid removal unit in fluid communication with and coupled between the conversion reactor and the slurry conversion unit and configured to separate a bottoms product comprising tars and/or solids from at least a portion of the reactor effluent.

37. The system of any one of embodiments 35 to 36, comprising a product separation unit in fluid communication with and upstream of the slurry conversion unit and configured to separate a hydrogen product from the at least a portion of the reactor effluent.

38. The system of any one of embodiments 35 to 37, comprising a finishing acetylene conversion unit in fluid communication with the slurry conversion unit and configured to convert at least a portion of the acetylene in the vapor product from the slurry conversion unit into ethylene.

39. The system of any one of embodiments 35 to 38, comprising a polymerization unit in fluid communication with the slurry conversion unit and configured to convert at least a portion of the ethylene into polyethylene.

40. The system of any one of embodiments 35 to 39, wherein the conversion reactor is a regenerative reverse flow reactor that comprises:
   a reactor body, wherein the reactor body forms a reaction region within the reactor body;
   a packing material disposed at least partially within the reaction region; and one or more valve assemblies coupled to the reactor body and in flow communication with the reaction region and configured to control fluid flow of the at least a portion of the pyrolysis feed between a location external to the reactor body and within the reaction region.

41. The system of any one of embodiments 34 to 40 wherein the slurry conversion unit further comprises a plurality of heat exchange tubes disposed within the second interior region.

42. The system of embodiment 41, further comprising:
   a heat exchanger upstream of the conversion reactor and configured to heat one or more reactants upstream of the conversion reactor; and
   one or more conduits to pass a utility fluid to one or more of the plurality of heat exchange tubes in the slurry converter unit and pass the heated utility fluid from the slurry conversion unit and to heat exchanger to heat the one or more reactants.

43. The system of embodiment 41, further comprising:
   a heat exchanger upstream of the conversion reactor and configured to heat pyrolysis feed upstream of the conversion reactor; and
   one or more conduits to pass a utility fluid to one or more of the plurality of heat exchange tubes in the slurry converter unit and pass the heated utility fluid from the slurry conversion unit and to the heat exchanger to heat the pyrolysis feed.

44. A method for processing hydrocarbons to produce ethylene comprising:
   exposing a first pyrolysis feed to a peak pyrolysis gas temperature≥1500.0° C. within a first conversion reactor to produce a first reactor effluent;
   exposing a second pyrolysis feed to a peak pyrolysis gas temperature≥700.0° C. within a second conversion reactor to produce a second reactor effluent;
   combining the first reactor effluent with the second reactor effluent to produce a combined reactor effluent;
   combining acetylene, hydrogen, carrier fluid and catalytic particles to produce a slurry in a slurry conversion unit, wherein the acetylene is derived from the combined reactor effluent; and
   exposing the slurry to operating conditions that include an average hydrogenation reaction temperature greater than or equal to 125° C. to produce a vapor product comprising ethylene.

45. The method of embodiment 44, further comprising
   recovering heat from the slurry converter unit; and
   utilizing the recovered heat to reduce the amount of reactants provided to one or more of the first conversion reactor and second conversion reactor.

46. The method of any one of embodiments 44 and 45, further comprising separating a hydrocarbon feed into a first mixture and a second mixture, wherein the first pyrolysis feed is derived from the first mixture and the second pyrolysis feed is derived from the second mixture.

47. The method of embodiment 46, further comprising:
   heating a utility fluid in the slurry conversion unit via indirect heat exchange; and
   combining the heated utility fluid with the second mixture upstream of the second conversion reactor.

48. The method of any one of embodiments 44 to 47, further comprising:
heating a utility fluid in the slurry conversion unit via indirect heat exchange; and
heating one or more of the first pyrolysis feed and/or the second pyrolysis feed via the heated utility fluid.

49. The method of any one of embodiments 44 to 48, further comprising:
determining a first ethylene to acetylene mole ratio for the first reactor effluent;
determining a second ethylene to acetylene mole ratio for the second reactor effluent; and
adjusting the amount of recycle based on the determined first ethylene to acetylene ratio and the determined second ethylene to acetylene ratio.

50. An acetylene conversion method comprising:
combining acetylene, hydrogen, solvent and catalytic particles to produce a slurry in a slurry conversion unit, wherein the solvent is selective to absorb acetylene as compared to absorbing ethylene;
exposing the slurry to an average hydrogenation reaction temperature greater than or equal to 125° C. to produce a vapor product comprising ethylene; and
extracting heat from the slurry conversion unit via indirect heat exchange with a utility fluid.

51. An acetylene conversion method comprising:
exposing a pyrolysis feed to a peak pyrolysis gas temperature≥1500.0° C. within a conversion reactor to produce a reactor effluent;
adjusting an ethylene to acetylene mole ratio of the reactor effluent to have an ethylene to acetylene mole ratio less than or equal to 5:1;
passing the adjusted reactor effluent to a slurry conversion unit; and
producing ethylene from hydrogenation of at least a portion of the adjusted reactor effluent.

The principles and modes of operation of this invention have been described above with reference to various exemplary and preferred embodiments. As understood by those of skill in the art, the overall invention, as defined by the claims, encompasses other preferred embodiments not specifically enumerated herein.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

The invention claimed is:

1. An acetylene conversion method comprising:
combining acetylene, molecular hydrogen, carrier fluid and catalytic particles to produce a slurry having an acetylene concentration of at least 2 mol % in a slurry conversion unit; and
exposing the slurry to operating conditions that include a conversion rate of at least 2 moles/hour/cc of the catalyst particles and an average hydrogenation reaction temperature greater than or equal to 125° C. to produce a vapor product comprising ethylene; and
extracting heat from the slurry conversion unit via indirect heat exchange with a utility fluid.

2. A method of processing hydrocarbons to produce ethylene comprising:
combining (i) a first converter feed containing at least 2 mol % acetylene, based on the total first converter feed, and molecular hydrogen with (ii) a second converter feed comprising a carrier fluid and catalytic particles to produce slurry in a slurry conversion unit; and
reacting the acetylene with the molecular hydrogen in the presence of the catalytic particles in the slurry at operating conditions that include a conversion rate of at least 2 moles/hour/cc of the catalyst particles and an average hydrogenation reaction temperature greater than 125° C. to produce a vapor product comprising ethylene; and
extracting heat from the slurry conversion unit via indirect heat exchange with a utility fluid.

3. The method of claim 1, further comprising utilizing at least a portion of the extracted heat to perform one or more of (i) generating steam from the heated utility fluid, (ii) combining the heated utility fluid with a pyrolysis feed provided to a conversion reactor upstream of the slurry conversion unit, and (iii) heating the pyrolysis feed via the heated utility fluid.

4. The method of claim 1, further comprising utilizing at least a portion of the extracted heat to reduce one or more a pyrolysis feed and a combustion feed utilized in a conversion reactor upstream of the slurry conversion unit.

5. The method of claim 1, further comprising passing the utility fluid through a bank of heat exchange tubes within the slurry conversion unit to extract the heat.

6. The method of claim 1, wherein the utility fluid is one or more of water and steam.

7. The method of claim 1, further comprising:
removing at least a portion of the slurry from the slurry conversion unit;
regenerating the separated slurry; and
combining at least a portion of the regenerated slurry with the slurry in the slurry conversion unit.

8. The method of claim 1, further comprising:
separating at least a portion of the carrier fluid from the slurry in the slurry conversion unit;
regenerating the separated carrier fluid; and
utilizing at least a portion of the regenerated carrier fluid to produce the slurry.

9. The method of claim 1, further comprising exposing a pyrolysis feed to temperatures greater than 1500° C. under pyrolysis conditions to produce at least a portion of the acetylene provided to the slurry conversion unit.

10. The method of claim 1, wherein the slurry comprises between 2 wt % and 40 wt % catalyst particles based on the total weight of the slurry.

11. The method of claim 1, wherein the carrier fluid comprises a solvent that solubilizes green oil.

12. The method of claim 1, wherein the carrier fluid comprises a solvent that absorbs acetylene at a higher selectivity as compared to ethylene.

13. The method of claim 1, wherein the carrier fluid has a dipole moment in the range from 2.0 D to 4.0 D.

14. The method of claim 1, wherein the catalytic particles convert at least a portion of the acetylene to ethylene at operating conditions sufficient to yield a conversion rate of at least 5 moles/hour/cc of catalytic particles.

15. The method of claim 1, wherein the catalytic particles are in the form of spherical or semi-spherical particles having an average diameter ≤150 micrometers.

16. The method of claim 1, wherein the average hydrogenation reaction temperature is in the range of 200° C. to 300° C.

17. The method of claim 1, wherein the catalyst particles comprise a catalytic material that has an acetylene conversion in excess of 80% at operating conditions.

18. The method of claim 1, wherein the catalyst particles comprises particles having an average diameter in the range of ≥10 μm and <150 μm.

19. The method of claim 4, further comprising:
passing the combustion feed to the conversion reactor during a heating step; and
reacting the combustion feed to form combustion products and combustion heat within the conversion reactor;
removing the combustion products from the conversion reactor;
passing the pyrolysis feed to the conversion reactor; and
exposing the pyrolysis feed to the combustion heat within the conversion reactor to produce a reactor effluent comprising at least a portion of the acetylene.

20. The method of claim 19, further comprising separating the acetylene from the reactor effluent.

21. The method of claim 1, comprising passing the vapor product to a finishing acetylene conversion unit to convert any remaining acetylene in the vapor product to ethylene.

22. The method of claim 1, wherein each of the catalytic particles comprise at least 2 wt % of an active catalytic material comprised of one or more metals selected from Group 8 to 10 of the Periodic Table based on the total weight of the catalytic particle.

\* \* \* \* \*